(12) United States Patent
Engelbart et al.

(10) Patent No.: US 7,489,392 B2
(45) Date of Patent: Feb. 10, 2009

(54) SYSTEMS AND METHODS FOR USING LIGHT TO INDICATE INCONSISTENCY LOCATIONS ON A COMPOSITE STRUCTURE

(75) Inventors: Roger W. Engelbart, St. Louis, MO (US); Frank G. Speno, Glendale, MO (US)

(73) Assignee: The Boeing Company, Chicago, IL (US)

( * ) Notice: Subject to any disclaimer, the term of this patent is extended or adjusted under 35 U.S.C. 154(b) by 140 days.

(21) Appl. No.: 11/688,068

(22) Filed: Mar. 19, 2007

(65) Prior Publication Data
US 2007/0204555 A1    Sep. 6, 2007

Related U.S. Application Data

(63) Continuation-in-part of application No. 10/822,538, filed on Apr. 12, 2004, now Pat. No. 7,193,696.

(51) Int. Cl.
*G01N 21/00* (2006.01)
(52) U.S. Cl. ............... 356/237.1; 356/239.3; 356/237.2
(58) Field of Classification Search .... 356/237.1–241.6
See application file for complete search history.

(56) References Cited

U.S. PATENT DOCUMENTS

| | | | |
|---|---|---|---|
| 3,879,245 A | | 4/1975 | Fetherson et al. |
| 4,001,877 A | * | 1/1977 | Simpson ............... 348/191 |
| 4,037,971 A | * | 7/1977 | Belleson et al. ......... 356/237.5 |

(Continued)

FOREIGN PATENT DOCUMENTS

EP     0319797    6/1989

(Continued)

OTHER PUBLICATIONS

Pending U.S. Appl. No. 10/949,848, filed Sep. 2004, Stulc.

(Continued)

*Primary Examiner*—L. G Lauchman
*Assistant Examiner*—Jarreas C Underwood
(74) *Attorney, Agent, or Firm*—Harness, Dickey & Pierce, P.L.C.

(57) ABSTRACT

A method for using light to indicate locations of inconsistencies on a composite structure. The method generally includes electronically accessing positional data defining one or more inconsistency locations on a composite structure. The positional data may be extracted from a part fabrication file containing numerical control (NC) data that may be used by a material placement machine to fabricate the composite structure. A light source directs light at the composite structure to illuminate the inconsistency locations as defined by the positional data. The information needed by the light source may be stored in a lookup table accessed by a processor of a vision detection system. The light allows the inconsistency locations to be noted for later action. Information such as the specific type of inconsistency detected, its dimensions, and a recommended course of action may all be projected via optical signals simultaneously onto the composite structure to aid the user in quickly identifying and evaluating each noted inconsistency. The lookup table may also be used to store historical information that aids in the evaluation of specific types of inconsistencies and may be used to by the system to suggest specific type(s) of action to the user in addressing each inconsistency.

27 Claims, 22 Drawing Sheets

U.S. PATENT DOCUMENTS

| | | | |
|---|---|---|---|
| 4,064,534 | A | 12/1977 | Chen et al. |
| 4,310,132 | A | 1/1982 | Robinson et al. |
| 4,400,618 | A * | 8/1983 | Bupp et al. ............. 250/302 |
| 4,548,859 | A | 10/1985 | Kline et al. |
| 4,608,220 | A | 8/1986 | Caldwell et al. |
| 4,693,678 | A | 9/1987 | Von Volkli |
| 4,699,683 | A | 10/1987 | McCowin |
| 4,760,444 | A | 7/1988 | Nielson et al. |
| 4,780,262 | A | 10/1988 | Von Volkli |
| 4,790,898 | A | 12/1988 | Woods |
| 4,830,298 | A | 5/1989 | Van Blunk |
| 4,877,471 | A | 10/1989 | McCowin et al. |
| 4,941,182 | A | 7/1990 | Patel |
| 5,024,399 | A | 6/1991 | Barquet et al. |
| 5,058,497 | A | 10/1991 | Bishop et al. |
| 5,153,668 | A | 10/1992 | Katzir et al. |
| 5,198,983 | A | 3/1993 | Blake et al. |
| 5,337,647 | A | 8/1994 | Roberts et al. |
| 5,439,549 | A | 8/1995 | Fryc et al. |
| 5,450,147 | A | 9/1995 | Dorsey-Palmateer |
| 5,518,208 | A | 5/1996 | Roseburg |
| 5,540,126 | A | 7/1996 | Piramoon |
| 5,562,788 | A | 10/1996 | Kitson et al. |
| 5,651,600 | A | 7/1997 | Dorsey-Palmateer |
| 5,683,646 | A | 11/1997 | Reilling, Jr. |
| 5,700,337 | A | 12/1997 | Jacobs et al. |
| 5,746,553 | A | 5/1998 | Engwall |
| 5,804,276 | A | 9/1998 | Jacobs et al. |
| 5,814,386 | A | 9/1998 | Vasiliev et al. |
| 5,822,055 | A | 10/1998 | Tsai et al. |
| 5,825,495 | A | 10/1998 | Huber |
| 5,871,117 | A | 2/1999 | Protasov et al. |
| 5,917,588 | A | 6/1999 | Addiego |
| 5,949,901 | A | 9/1999 | Nichani et al. |
| 5,963,660 | A | 10/1999 | Koontz et al. |
| 5,979,531 | A | 11/1999 | Barr et al. |
| 6,012,883 | A | 1/2000 | Engwall et al. |
| 6,013,341 | A | 1/2000 | Medvedev et al. |
| 6,045,651 | A | 4/2000 | Kline et al. |
| 6,074,716 | A | 6/2000 | Tsotsis |
| 6,075,883 | A | 6/2000 | Stern et al. |
| 6,086,696 | A | 7/2000 | Gallagher |
| 6,112,792 | A | 9/2000 | Barr et al. |
| 6,168,358 | B1 | 1/2001 | Engwall et al. |
| 6,184,924 | B1 | 2/2001 | Scneider et al. |
| 6,205,239 | B1 | 3/2001 | Lin et al. |
| 6,246,788 | B1 * | 6/2001 | Pattikonda et al. ........... 382/147 |
| 6,288,780 | B1 | 9/2001 | Fairley et al. |
| 6,364,250 | B1 | 4/2002 | Brinck et al. |
| 6,369,492 | B1 | 4/2002 | Sugimoto |
| 6,369,899 | B1 * | 4/2002 | Hamada ............. 356/603 |
| 6,390,169 | B1 | 5/2002 | Johnson |
| 6,451,152 | B1 | 9/2002 | Holmes et al. |
| 6,480,271 | B1 | 11/2002 | Cloud et al. |
| 6,639,660 | B1 * | 10/2003 | Beck et al. .............. 356/237.2 |
| 6,642,960 | B1 * | 11/2003 | Kohashi et al. ............. 348/246 |
| 6,648,273 | B2 | 11/2003 | Anast |
| 6,692,681 | B1 | 2/2004 | Lunde |
| 6,725,123 | B1 | 4/2004 | Denueli |
| 6,799,619 | B2 | 10/2004 | Holmes et al. |
| 6,814,822 | B2 | 11/2004 | Holmes et al. |
| 6,871,684 | B2 | 3/2005 | Engelbart et al. |
| 6,937,753 | B1 | 8/2005 | O'Dell et al. |
| 7,039,485 | B2 | 5/2006 | Engelbart et al. |
| 7,048,024 | B2 | 5/2006 | Clark |
| 7,080,441 | B2 | 7/2006 | Braun |
| 7,083,698 | B2 | 8/2006 | Engwall |
| 7,134,629 | B2 | 11/2006 | Johnson et al. |
| 7,137,182 | B2 | 11/2006 | Nelson |
| 7,193,696 | B2 | 3/2007 | Engelbart |
| 7,228,611 | B2 | 6/2007 | Anderson |
| 7,236,625 | B2 | 6/2007 | Engelbart et al. |
| 2001/0002149 | A1 | 5/2001 | Vaezs-Iravani et al. |
| 2001/0023349 | A1 | 9/2001 | Van Tassel et al. |
| 2002/0141632 | A1 | 10/2002 | Engelbart et al. |
| 2002/0176617 | A1 | 11/2002 | Simonetti |
| 2003/0090669 | A1 * | 5/2003 | Jung et al. ............. 356/450 |
| 2003/0230178 | A1 | 12/2003 | Steadman |
| 2004/0194506 | A1 | 10/2004 | Ueda et al. |
| 2005/0030527 | A1 | 2/2005 | Reinhorn |

FOREIGN PATENT DOCUMENTS

| | | |
|---|---|---|
| EP | 0833146 | 4/1998 |
| EP | 0903574 | 3/1999 |
| EP | 1 030172 | 8/2000 |
| JP | 2001012930 | 1/2001 |
| WO | WO 2004/025385 | 3/2004 |

OTHER PUBLICATIONS

Pending U.S. Appl. No. 60/559,911, filed Apr. 2004, Johnson et al.
Pending U.S. Appl. No. 10/628,691, filed Jul. 2003, Engelbart et al.
Pending U.S. Appl. No. 10/646,509, filed Aug. 2003, Johnson.
Pending U.S. Appl. No. 10/726,099, filed Dec. 2003, Engelbart et al.
U.S. pending patent application No. (not yet assigned) entitled: Composite Barrell Sections For Aircraft Fuselages and Other Structures, and Methods and Systems for Manufacturing Such Barrel Sections, May 20, 2004, Biornstad.
Sharp et al.; "Material Selection/Fabrication Issues for Thermoplastic Fiber Placement", *Journal of Thermoplastic Composite Materials*, vol. 8; Jan. 1995, p. 2-14.
http://www.cinmach.com/WolfTracks_4_1/MTG_WT7.htm; Premier 1 Features lighter, Stronger All-Composite Fuselage, 3 pages.
http://www.cinmach.comcompnews/PressReleases/pr00-11.htm; Raytheon Aircraft Orders Four More Fiber Cincinnati Fiber Placement Systems for Industry's First Composite-Fuselage Business Jets, 2 pages.
http://www.rockymountaincomposites.com/wind_sys.htm; Filament Winding, 2 pages.
Krupka R; Walz T; Ettemeyer A: Industrial Applications of Shearography for Inspection of Aircraft Components Proceedings of the 8th European Conference of Nondestructive Testing, Barcelona (Spain), Jun. 17-21, 2002, 'Online! Jun. 30, 2002, XP002351899 NDT.NET—Feb. 2003, vol. 8, No. 2 retrieved from the internet: URL:http://www.ndt.net/article/ecndt02/484/484.htm> retrieved on Oct. 31, 2005.
Prof. J. Zhang: "Angewandte Sensorik" Ch. 4, Sensoren in Der Robotik, Nov. 11, 2003, pp. 76-113, XP002327793; URL:http://tech-www.informatik.uni-hamburg.de/lehre/ws2003/vorle-sungen/angewandte_sensorik/vorlesung_03.pdf>, retrieved on Apr. 2004, p. 89.
European Search Report, Application No. 04076900.2, dated Dec. 1, 2004, 4 pages.
Advanced Technology Tape Laying for Affordable Manufacturing of Large Composite Structures; http://cinmach.com/tech/pdf/TapeLaying_Grimshaw.pdf; Michael N. Grimshaw, et al; 11 pages.
Fiber Placement; http://cinmach.com/tech/pdf/asm_chapter_fp.pdf; Don O. Evans; Cincinnati Machine; 3 pages.
Fiedler, L., et al, "Tango composite Fuselage Platform", Sampe Journal, vol. 39, No. 1, Jan./Feb. 2003, pp. 57-63.
BAe 146, Flight International, May 2, 1981, 2 pages.
A Barrelful of Experience, Intervia, May 1992, 2 pages.
Raytheon, Mar. 2000, vol. 4, No. 2, http://www.cts.com/king/vasci/newsletter/vol 42.html.
Automated Tape Laying; http://cinmach.com/tech/pdf/Grimshaw%20ASM%20Handbook.pdf; Michael N. Grimshaw; Cincinnati Machine; 6 pages.
Raytheon Aircraft's Hawker Horizon Reaches Fuselage Milestone, Raytheon News Release; http://www.beechcraft.de/Presse/2000/100900b.htm; 2 pages.
Business Aviation, Jun. 7, 2002, Http://www.aviationnow.com./avnow/news/channel_busav.jsp?view=story&id=news/btoyo0607.xml.

Beechcraft's Composite Challenge, http://www.aerotalk.com/Beech.cfm.

Evans, Don O., "Fiber Placement", 3 pages, Cincinnati Machine, pp. 477-479.

Bruckstein, et al, "Ominview Cameras with curved Surface Mirrors", Omnidirectional Vision 2000 Proceedings, IEEE Workshop, Jun. 2000.

* cited by examiner

```
G64.2X-56.0128Y-6.49622Z-43.784H-.088088H-.009956H-.996063D-.115166D.993346D.000256 F400$
N1[Q1:00]366.32X-26.8988Y-2.8717Z-43.7839H-.088203H-.008874H-.996063D-.115166D.993346D.000256 T[] F200{}$
N2G67X-26.8988Y-2.8717Z-43.7839H-.088203H-.008874H-.996063D-.102968D.994685D.000256 L.3075 R.3564$
N3G67X-26.933Y-2.5415Z-43.7838H-.088305H-.007791H-.996063D-.090754D.995873D.000256 L.3075 R.3564$
N4G67X-26.9631Y-2.2108Z-43.7837H-.088394H-.006707H-.996063D-.078526D.996912D.000256 L.3075 R.3564$
N5G67X-26.9892Y-1.8799Z-43.7836H-.088469H-.005621H-.996063D-.066286D.997801D.000256 L.3076 R.3564$
N6G67X-27.0112Y-1.5486Z-43.7836H-.088531H-.004535H-.996063D-.054036D.998539D.000256 L.3076 R.3565$
N7G67X-27.0291Y-1.2177Z-43.7835H-.088558H-.003448H-.996063D-.041779D.999127D.000256 L.3076 R.3565$
N8G67X-27.043Y-.8853Z-43.7834H-.088615H-.002361H-.996063D-.029515D.999564D.000256 L.3076 R.3565$
N9G67X-27.0528Y-.5534Z-43.7833H-.088637H-.001274H-.996063D-.017246D.999851D.000256 L.3076 R.3565$
N10[G67X-27.0585Y-.2214Z-43.7832H-.088646H-.000186H-.996063D-.004975D.999988D.000256 L.3076 R.3565$
N11G67X-27.0602Y.1107Z-43.7831H-.088641H.000902H-.996063D.007297D.999973D.000256 L.3076 R.3565$
N12G67Y.1163D.007502D.999972D.000238 T[18] L.0052 R.06$
N13G67X-27.0578Y.4428Z-43.783H-.088623H.001991H-.996063D.019568D.999809D.000256 L.3025 R.3505$
N14G67X-27.0513Y.7748Z-43.7829H-.088592H.003077H-.996063D.031836D.999493D.000256 L.3076 R.3565$
N15G67X-27.0407Y1.1067Z-43.7829H-.088547H.004164H-.996063D.044099D.999027D.000256 L.3077 R.3566$
N16G67X-27.026Y1.4385Z-43.7828H-.088489H.00525H-.996063D.056355D.998411D.000256 L.3077 R.3566$
N17G67X-27.0073Y1.7702Z-43.7827H-.088418H.006336H-.996063D.068603D.997644D.000256 L.3077 R.3566$
N18G67X-26.9845Y2.1015Z-43.7826H-.088333H.007422H-.996063D.08084D.996727D.000256 L.3077 R.3566$
N19G67X-26.9577Y2.4326Z-43.7825H-.088235H.008504H-.996063D.093066D.99566D.000256 L.3077 R.3566$
N20G67X-26.9268Y2.7633Z-43.7824H-.088124H.009586H-.996063D.105277D.994443D.000256 L.3077 R.3566$
N21G67X-26.8918Y3.0937Z-43.7823H-.087999H.010667H-.996063D.117473D.993076D.000256 L.3077 R.3566$
N22G67X-26.8528Y3.4235Z-43.7823H-.087861H.011746H-.996063D.129651D.991156D.000256 L.3077 R.3566$
N23G67X-26.8097Y3.7529Z-43.7822H-.08771H.012823H-.996064D.141809D.989894D.000256 L.3078 R.3567$
N24G67X-26.7626Y4.0818Z-43.7821H-.087546H.013898H-.996064D.153946D.988079D.000256 L.3078 R.3567$
N25G67X-26.7114Y4.4101Z-43.782H-.087368H.014971H-.996064D.16606D.986116D.000256 L.3078 R.3567$
N26G67X-26.6563Y4.7377Z-43.7819H-.087178H.016042H-.996064D.178148D.984004D.000256 L.3078 R.3567$
```

Send Current Course number to Inspection System — 416

Send Current Block number to Inspection System

Send NC Blocks numbers (Nxx) associated with gap inconsistency. — 428

403, 405

H Vector is the surface normal
D Vector is the path tangential vector

↳ Retract and Approach motion between courses.

FIG. 7

SYSTEMS AND METHODS FOR USING LIGHT TO INDICATE INCONSISTENCY LOCATIONS ON A COMPOSITE STRUCTURE

CROSS-REFERENCE TO RELATED APPLICATIONS

This application is a continuation-in-part of U.S. patent application Ser. No. 10/822,538 filed on Apr. 12, 2004, and presently allowed. The disclosure of the above application is incorporated herein by reference.

FIELD

The present disclosure relates generally to the fabrication of composite structures with material placement machines. More particularly (but not exclusively), the present disclosure relates to systems and methods for using light to indicate manufacturing inconsistency locations on a composite structure, such as the locations of manufacturing inconsistencies detected by an in-process vision inspection system during fabrication of the composite structure.

Composite structures have been known in the art for many years. Although composite structures can be formed in many different manners, one advantageous technique for forming composite structures is an automated material placement process, such as an automated fiber placement or automated collation process described in U.S. patent application Ser. No. 10/068,735, filed on Feb. 6, 2002, entitled "Composite Material Collation Machine and Associated Method for High Rate Collation of Composite Materials". The contents of U.S. patent application Ser. No. 10/068,735 are incorporated herein by reference in its entirety as if fully set forth herein.

BACKGROUND

In an automated collation technique, one or more ribbons of composite material (also known as composite strands or tows) are laid down on a substrate with a material placement machine. The substrate may be a tool or mandrel, but can also be formed of one or more underlying layers of composite material that have been previously laid down and compacted.

Fiber placement processes typically utilize a heat source to assist in compaction of the plies of composite material at a localized nip point. In particular, the ribbon or tow of composite material and the underlying substrate are heated at the nip point to increase the tack of the resin of the plies while being subjected to compressive forces to ensure adhesion to the substrate. To complete the part, additional strips of composite material can be applied in a side-by-side manner to form layers and can be subjected to localized heat and pressure during the consolidation process.

Unfortunately, manufacturing inconsistencies can occur during the placement of the composite strips onto the underlying composite structure. Such inconsistencies can include tow gaps, overlaps, dropped tows, puckers (i.e., raised regions in a tow), and twists. In addition, foreign objects and debris (FOD), such as resin balls and fuzz balls, can accumulate on a surface of the composite structure which must be detected, identified and eventually removed from the ply surface.

Composite structures fabricated by automated material placement methods typically have specific maximum allowable size requirements for each inconsistency, with these requirements being established by the production program. Production programs also typically set well-defined accept/reject criteria for maximum allowable number of (i.e., density) of inconsistencies per-unit area and maximum allowable cumulative inconsistencies width-per-unit area.

To ensure that the composite laminates fabricated by fiber placement processes satisfy the requirements pertaining to inconsistency size, the structures are typically subjected to a 100% ply-by-ply visual inspection. These inspections are traditionally performed manually during which time the fiber placement machine is stopped and the process of laying materials halted until the inspection and subsequent actions to address or rework the inconsistency, if any, are completed. In the meantime, the fabrication process has been disadvantageously slowed by the manual inspection process and machine downtime associated therewith.

Recently, systems and methods have been developed that are capable of detecting, measuring, and marking individual inconsistencies in the composite structure. Exemplary systems and methods capable of accurately and reliably detecting, measuring and/or marking inconsistencies in a composite structure are disclosed in U.S. Pat. No. 7,171,033, issued Jan. 30, 2007; U.S. Pat. No. 6,871,684 issued Mar. 29, 2005; and U.S. patent application Ser. No. 10/628,691, filed Jul. 28, 2003. The entire disclosures of the above documents are each incorporated herein by reference as if fully set forth herein.

Systems and methods have also been developed which are capable of determining an inconsistency characteristic representative of the composite structure, such as an inconsistency density-per-unit area and/or cumulative inconsistency width-per-unit area. Exemplary systems and methods capable of determining inconsistency characteristics are disclosed in U.S. patent application Ser. No. 10/726,099, filed Dec. 2, 2003, the entire contents of which are incorporated herein by reference as if fully set forth herein.

Systems and methods have also been developed which enable a material placement machine to automatically return to inconsistencies for manually addressing the inconsistencies, and/or that enable the machine to automatically return to and address inconsistencies without operator intervention. Exemplary systems and methods are disclosed in U.S. Pat. No. 7,039,485, issued May 2, 2006, the entire contents of which are incorporated herein by reference as if fully set forth herein.

The above-mentioned inspection systems and methods have worked well for their intended purposes and have reduced unproductive downtime associated with inspection and the actions needed to address the inconsistency in the laminate plies. The inventors hereof have recognized, however, that such systems and methods can be even further improved by providing suitable non-contact marking alternatives to ink-based surface marking systems. By way of background, ink-based marking systems can employ various means, such as inkjet marking, pump-fed felt-tip marker, spring loaded marking pen, among others, to deposit an amount of ink onto the composite structure in those areas where inconsistencies have been detected. With these ink-based marking systems, the ink should be carefully selected to ensure compatibility with the composite substrate and to ensure that the ink doesn't contaminate the composite substrate. The ink should also be low enough in viscosity so that it flows freely through the supply lines and the sprayer nozzle. The solvents used in the ink should also allow the ink to dry quickly enough to carefully select an ink satisfying all of the conditions and can require significant amounts of time and costs.

SUMMARY

The present disclosure relates to systems and methods capable of using light to indicate inconsistency locations on a composite structure, such as the locations of inconsistencies detected by an in-process vision inspection system during fabrication of the composite structure.

In one implementation a method generally includes electronically accessing positional data defining one or more inconsistency locations on a composite structure. The method also includes automatically causing at least one light source to direct light at the composite structure to indicate the inconsistency location(s) as defined by the positional data. Accordingly, the light allows the inconsistency location(s) to be readily ascertained for later action, for example to rework the inconsistency to remove it.

In another implementation a system generally includes at least one light source and a controller operatively associated with the light source. The controller is capable of electronically accessing positional data defining one or more inconsistency locations on the composite structure. Without operator assistance, the controller can automatically cause the light source to direct light at the composite structure to indicate the inconsistency location(s) as defined by the positional data.

In another implementation a program generally includes a computer executable module for electronically accessing positional data defining one or more inconsistency locations on the composite structure. The program also includes a computer executable module for automatically generating instructions for automatically causing at least one light source to direct light at the composite structure to indicate the inconsistency location(s) as defined by the positional data.

In still another implementation a vision inspection computer and a light projection computer are provided as part of a system for controlling a light source to direct an optical signal onto a composite structure being manufactured. The optical signal provides a plurality of types of information to the user regarding a detected inconsistency. In one specific implementation a first portion of the optical signal is directed onto the inconsistency to illuminate the inconsistency. A second portion of the optical signal projects information such as text, indicia, a graphic or a symbol obtained from the lookup table onto the surface of the composite structure. The text, indicia, graphic or symbol indicates the specific type of inconsistency present. Accordingly, the user is visually apprised of not only the location of the inconsistency but the specific type of inconsistency as well.

Further embodiments involve using the lookup table to store information regarding the dimensions of each detected inconsistency as well as historical information concerning different types of inconsistencies and the types of actions that have been successful in addressing (i.e., reworking) various types of inconsistencies. This information is also projected onto the composite structure by using a portion of the optical signal from the light source. The information visually apprises the user of the dimensions of the inconsistency and provides a recommended action for addressing the inconsistency. The historical information may also be used to cause a portion of the optical signal to project a word, indicia or symbol onto the composite structure at a position adjacent to the inconsistency being highlighted, that indicates to the user that no action needs to be taken for that particular type of inconsistency.

The features, functions and advantages can be achieved independently in various embodiments of the present disclosures or may be combined in yet other embodiments.

BRIEF DESCRIPTION OF THE DRAWINGS

The present disclosure will become more fully understood from the detailed description and the accompanying drawings, wherein

FIG. 6 illustrates an exemplary block of numerical control (NC) data within a part fabrication file for a material placement machine;

FIG. 7 illustrates an exemplary block of NC code for generating corresponding retract and approach motions of the material placement machine between courses;

DETAILED DESCRIPTION

The following description of the various embodiments is merely exemplary in nature and is in no way intended to limit the disclosure, its application, or uses.

The present disclosure provides systems and methods for using light to indicate locations of inconsistencies on a composite structure. In one implementation, a method generally includes electronically accessing positional data defining one or more inconsistency locations on a composite structure. The positional data can be extracted from a part fabrication file in which resides numerical control (NC) data that can be used by a material placement machine in fabricating the composite structure. The positional data can define one or more locations on the composite structure at which inconsistencies have been detected, such as dropped tows, tow gaps, foreign objects and debris (FOD), puckers, etc.

The method may include automatically causing (e.g., activating, steering, light splitting, etc.) at least one light source (e.g., a laser projection device, laser pointer, etc.) to direct an optical signal at the composite structure to indicate (e.g., illuminate, highlight, circumscribe, etc.) the inconsistency location(s) as defined by the positional (i.e., coordinate) data. The optical signal (e.g., light) allows the inconsistency locations to be readily ascertained for later action, for example to rework the inconsistency so that it is removed or otherwise addressed so that the composite structure meets predetermined manufacturing tolerances.

According to another aspect of the disclosure, a system generally includes at least one light source and a controller associated with the light source. The controller is capable of accessing positional data defining one or more inconsistency locations on the composite structure. Without operator assistance, the controller can automatically cause the light source to direct light at the composite structure to indicate the inconsistency location(s) as defined by the positional data.

Yet another aspect of the disclosure provides a program that generally includes a computer executable module for electronically accessing positional data defining one or more inconsistency locations on the composite structure. The program also includes a computer executable module for automatically generating instructions for automatically causing at least one light source to direct light at the composite structure to indicate the inconsistency location(s) as defined by the positional data.

Although aspects of the present disclosure can be described with a program having a direct effect on and direct control of one or more light sources, it should be understood that it is the instructions generated upon execution of the program, for example, by a processor of a control interface, and the subsequent implementation of such instructions by the processor, that have direct effect on and direct control of the light source(s).

Figure 1:
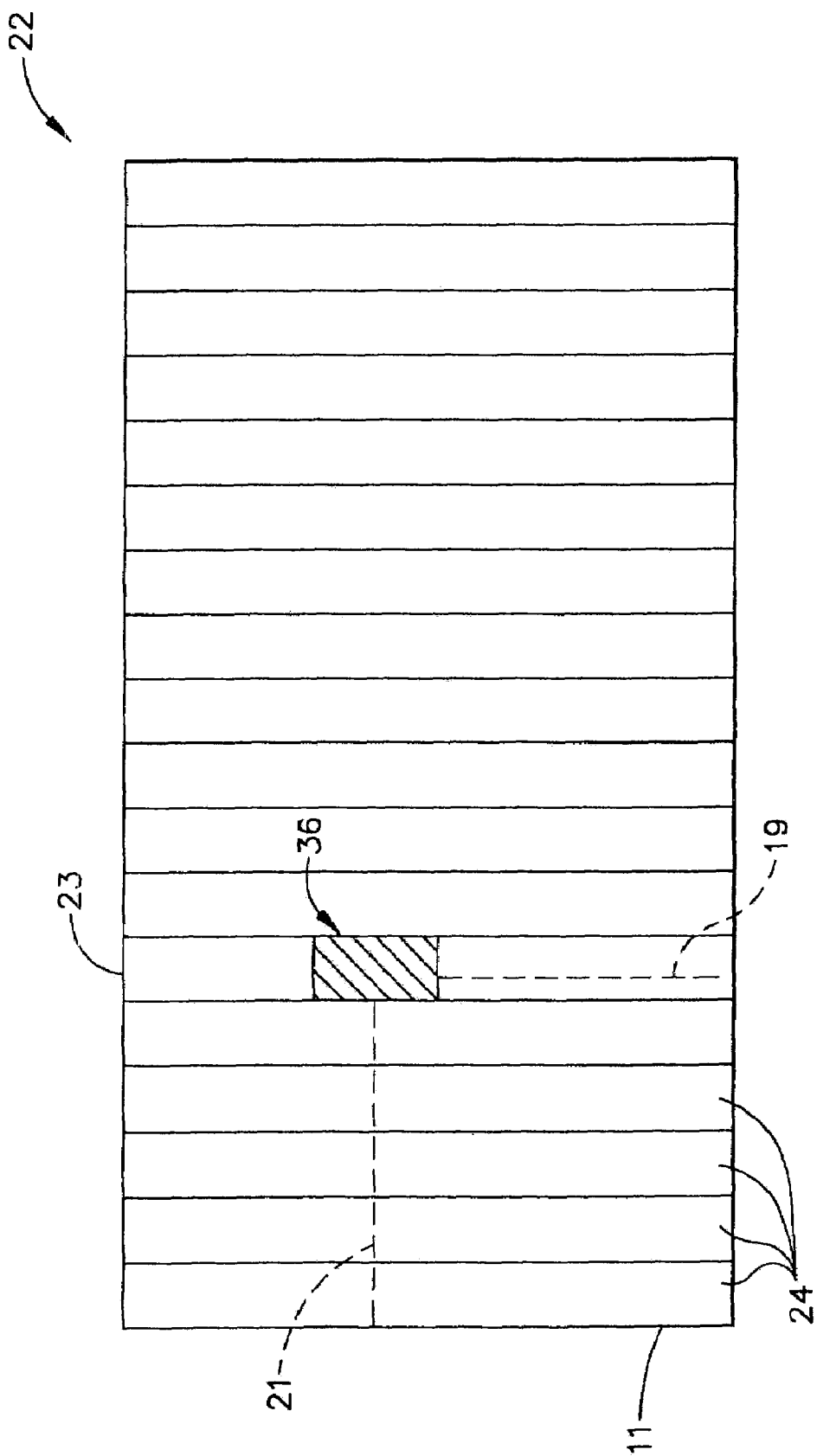
FIG. 1 is a schematic view of an exemplary composite structure illustrating linear and lateral distances to an inconsistency in the composite structure.

FIG. 1 illustrates an exemplary composite structure 22, which can include a plurality of layers or plies. Each ply is generally comprised of a plurality of adjacent tows or strips of composite tape 24. The strips 24 typically include a plurality of fibers embedded in a resin or other material that becomes tacky or flowable upon the application of heat. The strips 24 can be arranged on a work surface, such as a table, mandrel, or other tool 26 (FIG. 8), and compacted with a compaction roller 20 (FIG. 9) to form the composite structure 22 according to an automated collation technique, such as that described in U.S. patent application Ser. No. 10/068,735.

As shown in FIG. 1, eighteen courses or strips 24 have been completed by the material placement machine. That is, the material placement machine has made eighteen passes across a substrate. During each of the 18 passes the material placement machine lays down a strip 24 on the substrate. The sixth course 23 of the composite structure 22 includes an inconsistency 36 where a portion of a tow is missing. The dashed line 19 represents the linear distance along the sixth course 23 to the inconsistency 36. The dashed line 21 represents the lateral distance to the inconsistency 36 from a first end 11 of the composite structure 22.

Various implementations of the disclosure can be used with an inspection system capable of detecting, measuring, marking or displaying images of inconsistencies and/or establishing and retaining generally precise inconsistency locations. Such exemplary systems are described in U.S. patent application Ser. Nos. 09/819,922, 10/217,805, 10/628,691, 10/726,099, and/or 10/799,306.

Upon detection of an inconsistency, an inspection system can send a signal to trigger an ink-based marking device (e.g., inkjet marking, pump-fed felt-tip marker, spring-loaded marking pen, etc.) to place a visually prominent ink indication next to the inconsistency. In various implementations of the present disclosure, the signal for triggering the ink-based marking device may instead be used to trigger at least one light source to direct light at the composite structure to indicate an inconsistency location.

Figure 15:
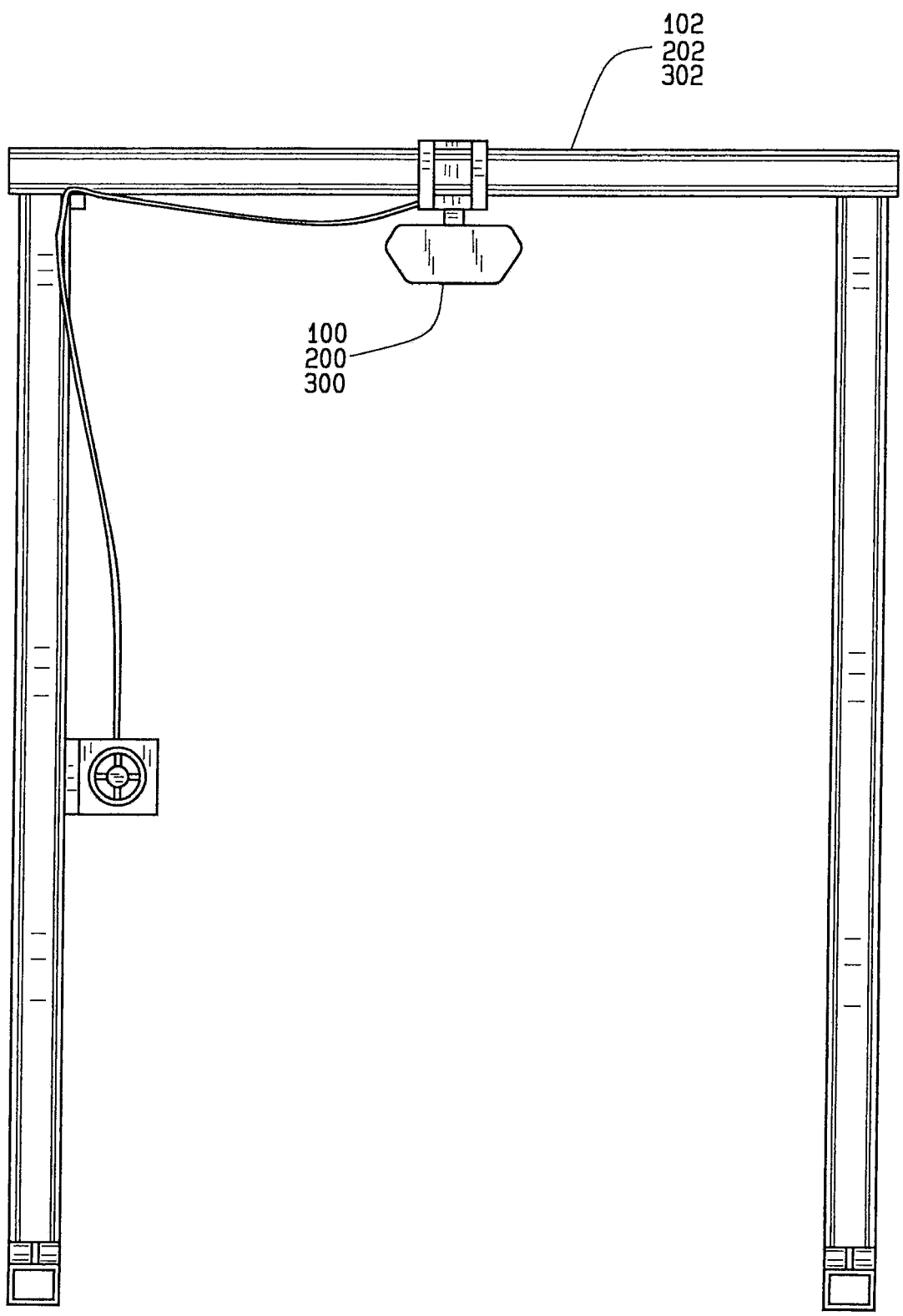
FIG. 15 is a perspective view of an exemplary gantry supporting a light source that can be used to indicate inconsistency locations on a composite structure according to another implementation of the present disclosure.

Various implementations may include mounting the light source to a stationary location adjacent the material placement machine and the work surface (e.g., tool 26 in FIG. 8, etc.) on which the composite structure is being fabricated. By way of example, FIG. 15 illustrates a light source 100, 200, 300 being supported by a framework or gantry 102, 202, 302 that may be independent or separate from the material placement machine. Alternatively, the light source can be mounted directly to a stationary portion of the material placement machine. Stationary mounting of the light source enables the light source to be positioned and calibrated relative to a specific reference point on the work surface on which the composite structure is being fabricated.

Figure 3:
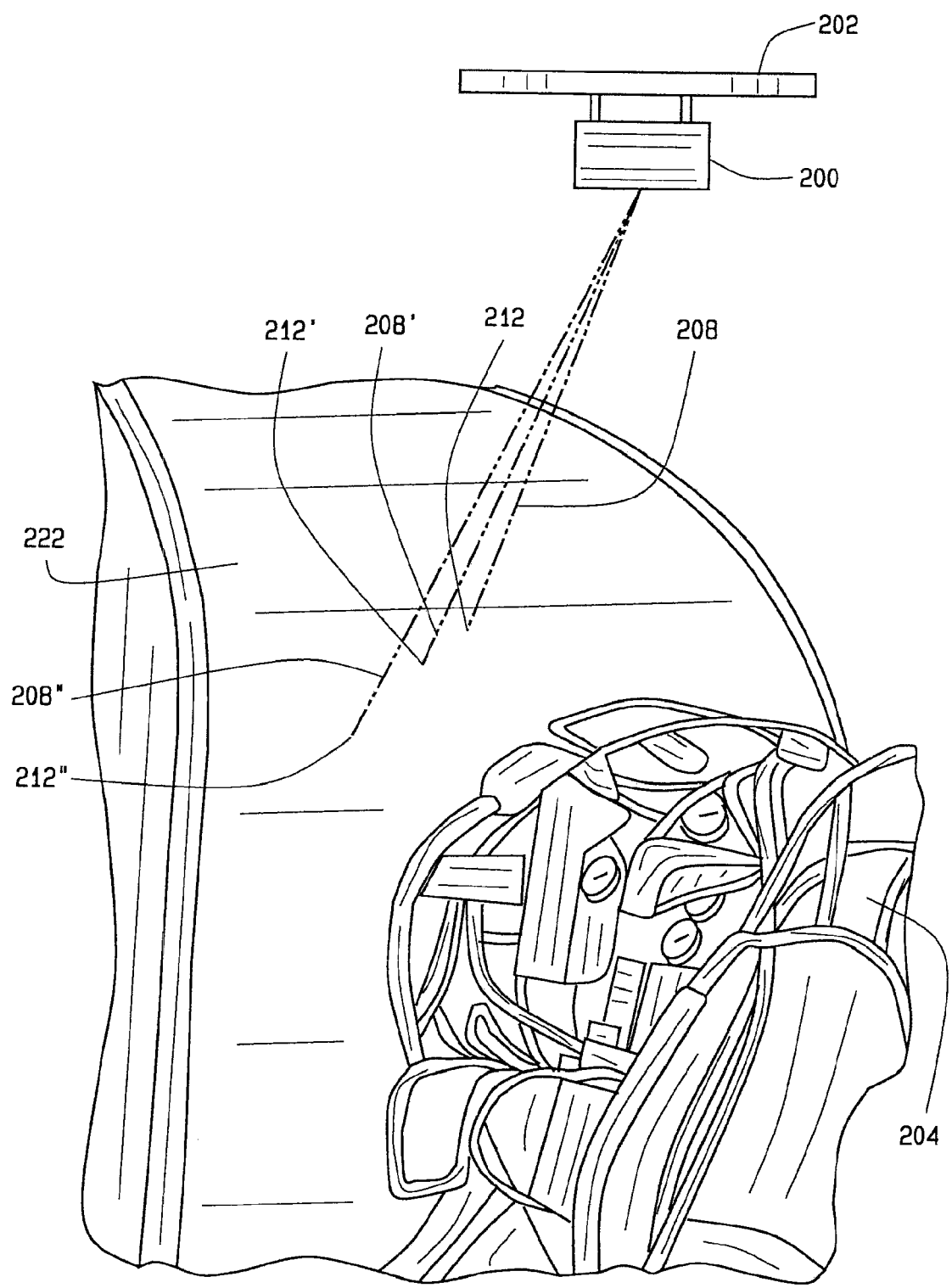
FIG. 3 is a perspective view of a light source indicating several inconsistency locations on a composite structure according to another embodiment on the disclosure.
Figure 4:
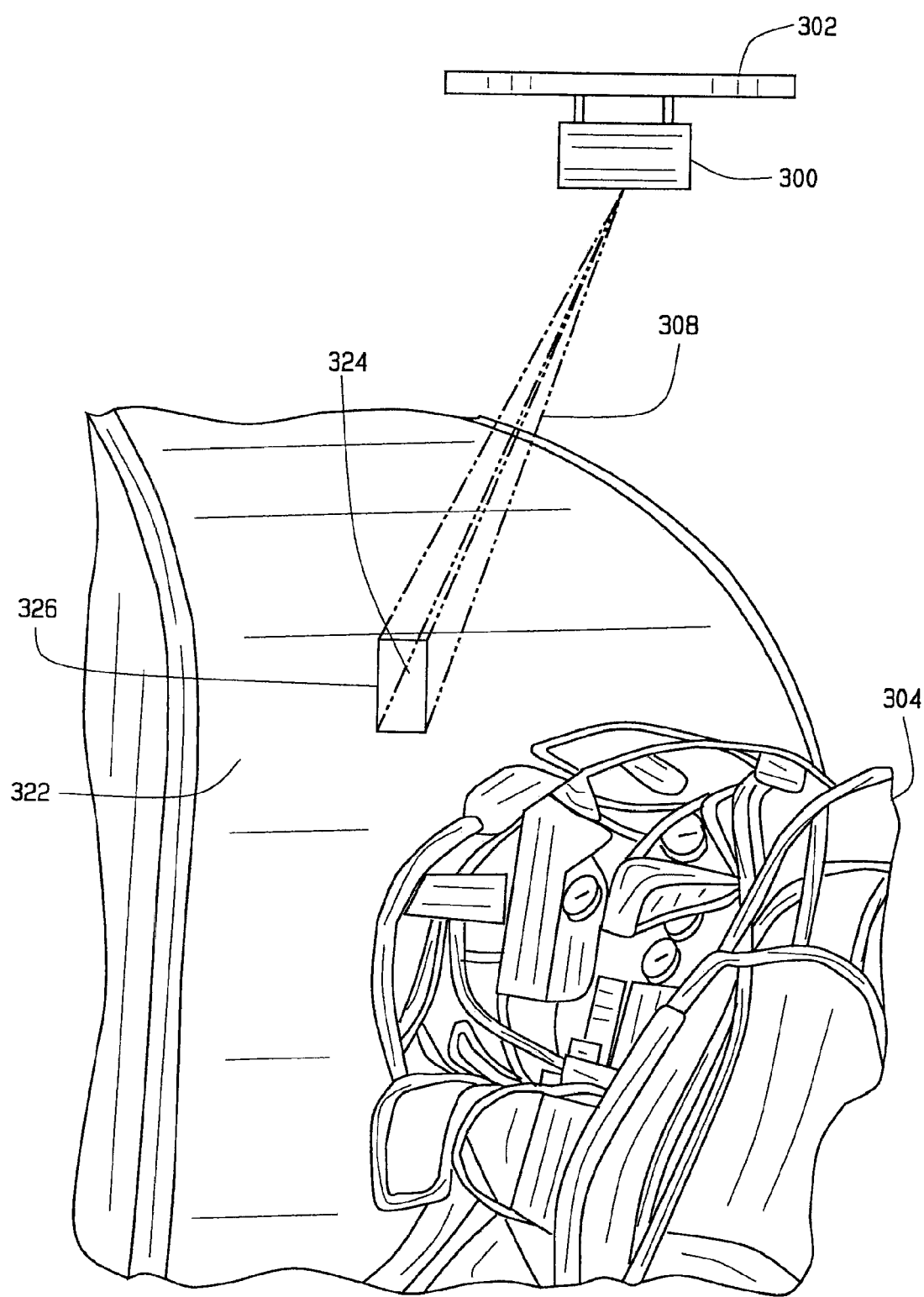
FIG. 4 is a perspective view of a light source indicating a region of a composite structure which includes one or more inconsistency locations according to another embodiment on the disclosure.

As described below, the light source may be adapted to project a single point (FIG. 2), multiple points (FIG. 3), or what appears to be a continuous line forming a boundary or template (e.g., box, circle, triangle, etc.) on the composite structure (FIG. 4). Locations to which the light is projected may be derived from coordinates taken from a computer-aided drawing (CAD) file. This CAD file may be created using various commercially available software programs. In an exemplary application, coordinates may be repetitive for the same part, assembly or laminate.

Positional or coordinate information defining inconsistency locations will change continuously based on the particular locations of the detected inconsistencies. Exemplary systems and methods for determining a location of an inconsistency on the laminate can include tracking course number and distance along a course by encoded positioning as described in U.S. patent application Ser. No. 10/726,099.

Upon detection of an inconsistency, a computer associated with the inspection system may signal a computer associated with the material placement machine to extract coordinate data from an appropriate numerical control (NC) block of the material placement program. This process is described generally below and in more detail in U.S. patent application Ser. No. 10/799,306. Extracted coordinate data may be maintained or stored to allow subsequent access thereto. For example, extracted coordinate data can be stored at least until placement of the current ply is completed and/or action is taken to address the inconsistency.

A control interface can be used to control and manage the transfer of coordinate data. The control interface can also control and manage the light source (e.g., activate, steer, etc.). In various implementations, coordinates can be converted to CAD format prior to their transfer to the control interface and used in steering the light source.

Figure 2:
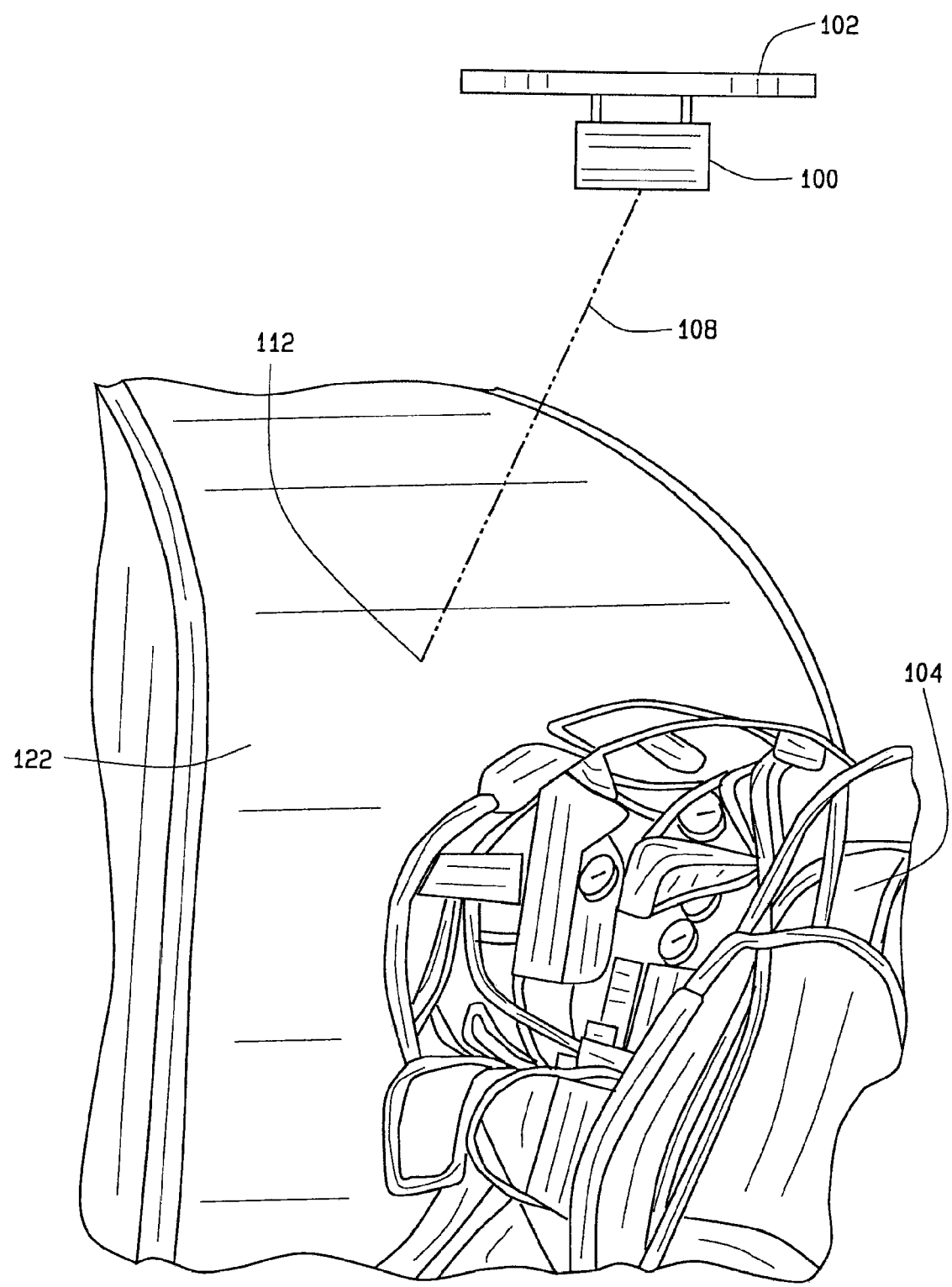
FIG. 2 is a perspective view of a light source indicating an inconsistency location on a composite structure according to an embodiment of the disclosure.

The actual marking or illumination by a light source to indicate inconsistency locations on the laminate can be accomplished in several ways, such as, the exemplary approaches shown in FIGS. 2 through 4. It should be noted, however, that FIGS. 2 through 4 are for purposes of illustration only and not for purposes of limitation. For example, FIGS. 2 through 4 each illustrate a laser projection device 100, 200 and 300 being used to indicate one or more inconsistency locations on a composite structure. But other implementations can include using any number of (i.e., one or more) light sources selected from a wide range of other suitable light source types besides a laser.

FIG. 2 illustrates a laser pointer or projection device 100 coupled to a stationary framework or gantry 102 at a position above and adjacent a robotic head unit 104 of a material placement machine. Alternatively, other mounting arrangements are possible for the laser projection device 100. For example, the laser projection device 100 can instead be mounted directly to a stationary portion of the material placement machine.

As shown, the laser projection device 100 is directing light 108 at an inconsistency location 112 on the composite structure 122, thereby illuminating the inconsistency location 112 and making it readily visible to an operator. Again, however, other suitable light sources besides a laser may be employed.

FIG. 2 generally represents a single sequential marking approach in which inconsistency coordinates are transferred in some predetermined order. Inconsistency locations can then be illuminated in a generally sequential fashion consistent with the transfer order such that only a single inconsistency location is illuminated at any given time.

Each inconsistency location can remain illuminated until disposition (e.g., inconsistency removal, FOD removal, etc.) is completed and the next set of coordinates is transferred. In response to the new coordinates, a controller can reposition or steer the laser projection device 100 such that the light therefrom no longer illuminates the location of the formerly present inconsistency, but instead illuminates the next inconsistency location as defined by the new coordinates.

In various implementations, an operator may manually address the inconsistency and/or remove FOD at the inconsistency location being illuminated. The operator may interface or communicate with the controller to indicate the completion of the manual operation. In response thereto, the controller may then extract the next set of coordinates for the next inconsistency location and cause the light source to illuminate that next inconsistency location as defined by the extracted coordinates.

In other implementations, however, inconsistencies can be addressed automatically by the material placement machine without requiring manual intervention by the user. In such implementations, a computer of the material placement machine can send an appropriate signal to the controller of the light source indicating completion of the action taken to address the inconsistency. Exemplary systems and methods for enabling automated action to address inconsistencies are described in U.S. patent application Ser. No. 10/799,306.

FIG. 3 illustrates a laser pointer or projection device 200 coupled to a stationary framework or gantry 202 at a position above and adjacent a robotic head unit 204 of a material placement machine. Alternatively, other mounting arrangements are possible for the laser projection device 200. For example, the laser projection device 200 can instead be mounted directly to a stationary portion of the material placement machine.

As shown, the laser projection device 200 is directing light 208, 208', and 208" at a composite structure 222 to simultaneously illuminate three inconsistency locations 212, 212', and 212" as defined by multiple coordinate sets. Other quantities (i.e., one or more) of inconsistency locations may also be illuminated at a given time depending on the particular application. And, one or more other suitable light sources besides a laser may also be employed.

In one embodiment the laser projection device 200 can be equipped with a splitter. The splitter causes light from the laser projection device 200 to be split and aimed to illuminate different inconsistency locations on the composite structure. As an alternative to splitting the light, various implementations can also include a plurality of light sources each capable of emitting light to indicate at least one different inconsistency location on the composite structure.

In various implementations, the laser projection device 200 can be configured to illuminate inconsistency locations only within a certain region or particularly sized area of the composite structure 222. Alternatively, the laser projection device 200 may instead be configured to illuminate inconsistency locations over the entire laminate.

The laser projection device 200 may continue to illuminate inconsistency locations until each inconsistency is addressed. Alternatively, coordinate information can be continuously updated such that an inconsistency location is no longer illuminated after the inconsistency has been addressed or otherwise removed. In such implementations, inconsistencies that have not been removed or that have not been fully addressed may be easily determined by simply noting which inconsistency locations remain illuminated.

FIG. 4 illustrates a laser pointer or projection device 300 coupled to a stationary framework or gantry 302 at a position above and adjacent a robotic head unit 304 of a material placement machine. Alternatively, other mounting arrangements are possible for the laser projection device 300. For example, the laser projection device 300 may instead be mounted directly to a stationary portion of the material placement machine.

As shown, the laser projection device 300 is indicating a specific area or region 324 of a composite structure 322 that includes one or more inconsistency locations. Light 308 from the laser projection device 300 appears to be a generally continuous line defining a box 326 on the composite structure 322. Alternatively, the laser projection device 300 can be configured to project light so as to form other suitable geometric shapes or outlines (e.g., circles, triangles, among others) on the composite structure 322.

Depending on the particular application, the light source can direct light at the composite structure to indicate the inconsistency location(s) only after the ply having the inconsistency location(s) is completed. Alternatively, the light source can instead direct light at the composite structure as inconsistencies are being detected during the fabrication of the composite structure. In either case, updated coordinates may be utilized as each new ply is being laid by the material placement machine.

In addition, a history file may be constructed to record information such as inconsistency rejections, inconsistency location coordinates, and the status of any action taken. The history file can reside, for example, within software associated with the inspection system, software associated with the material placement machine, a combination thereof, etc.

Optionally, various implementations of the disclosure can include illuminating inconsistency locations so as to indicate and distinguish among the locations of different types of inconsistencies. For example, an exemplary implementation can include using different types of light (e.g., light differing in color, intensity, hue, saturation, brightness, different lighted patterns, different lighted shapes or symbols, combinations thereof, among other attributes) to indicate and distinguish among the locations of different types of inconsistencies. By way of example only, blue-colored light may be used to indicate a location of foreign objects and debris (FOD) on the composite structure, while red-colored light is used to indicate a location of a dropped tow or tow gap. As another example, different colors of light can be used to indicate and distinguish between unacceptable inconsistencies and acceptable inconsistencies.

Various implementations of the disclosure can optionally include using light to not only indicate inconsistency locations, but also denote the category of acceptance criteria in which an inconsistency falls. For example, an exemplary implementation can include having light form one or more indicia, patterns, alphanumeric characters, symbols, colors, and/or combinations thereof, etc. on the composite so as to indicate and distinguish among one or more categories of acceptance criteria for inconsistencies. By way of background, a production program can specify for a part one or more different categories of acceptance criteria (e.g., maximum allowable number of inconsistencies per-unit area, maximum allowable cumulative inconsistency width-per-unit area, and maximum allowable width of a single inconsistency. For example, a first part region can be assigned category B which is more lenient than category A assigned to a second part region. The acceptance criteria within a category can be used for determining acceptability of an inconsistency within a region to which that category has been assigned.

By way of example only, an exemplary implementation may include having light to form a letter "A" at or near an inconsistency within a region of the part assigned category A acceptance criteria and/or to form a letter "B" at or near an inconsistency within another region of the part assigned category B, and so on. Using light to indicate and distinguish between categories of acceptance criteria enables the particular category of acceptance criteria for an inconsistency to be readily ascertained by an operator or other persons.

Figure 5A:
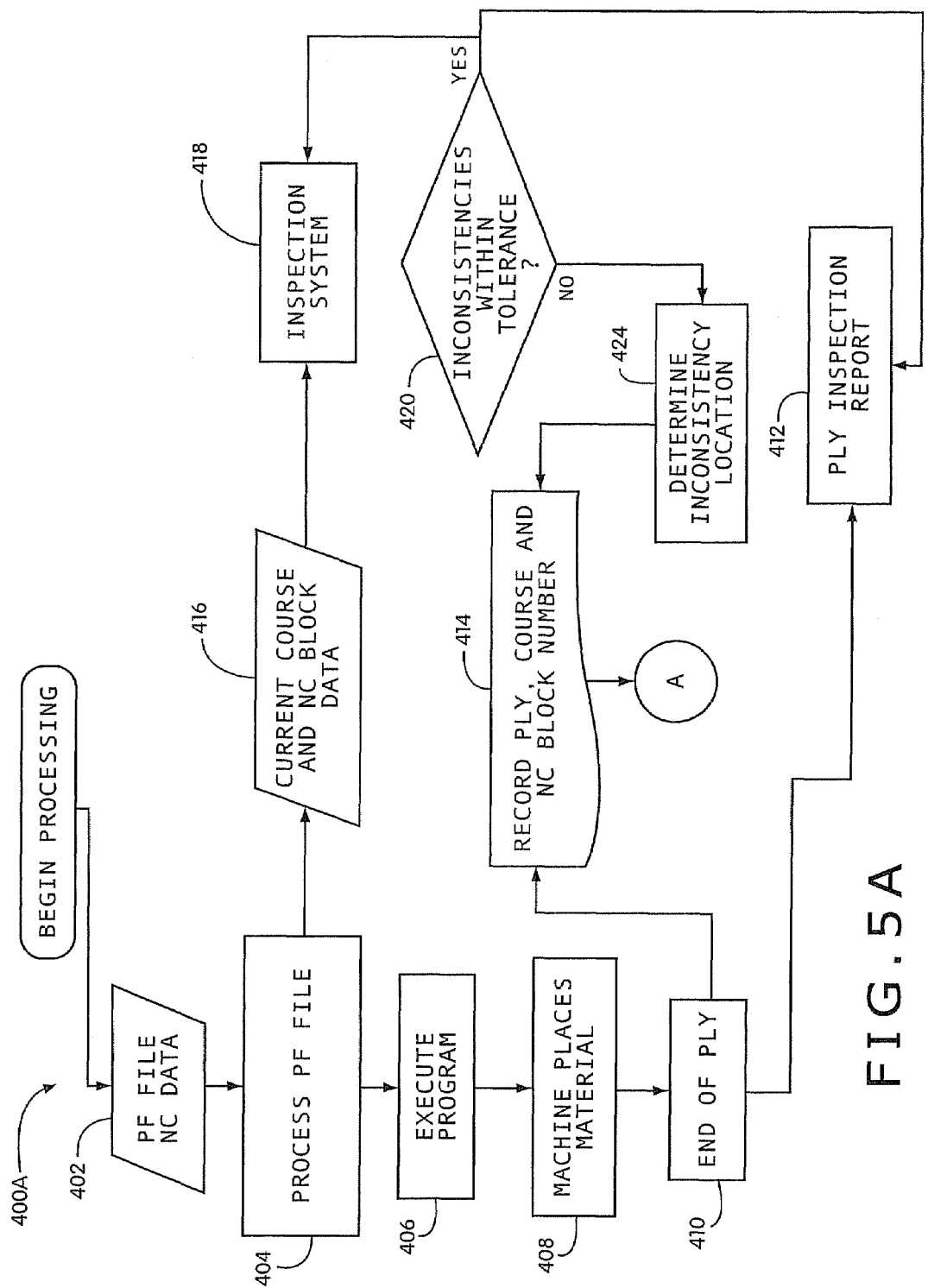
FIGS. 5A and 5B form a process flow diagram illustrating operations of a method for using light to indicate inconsistency locations on a composite structure according to one implementation of the present disclosure.
Figure 5B:
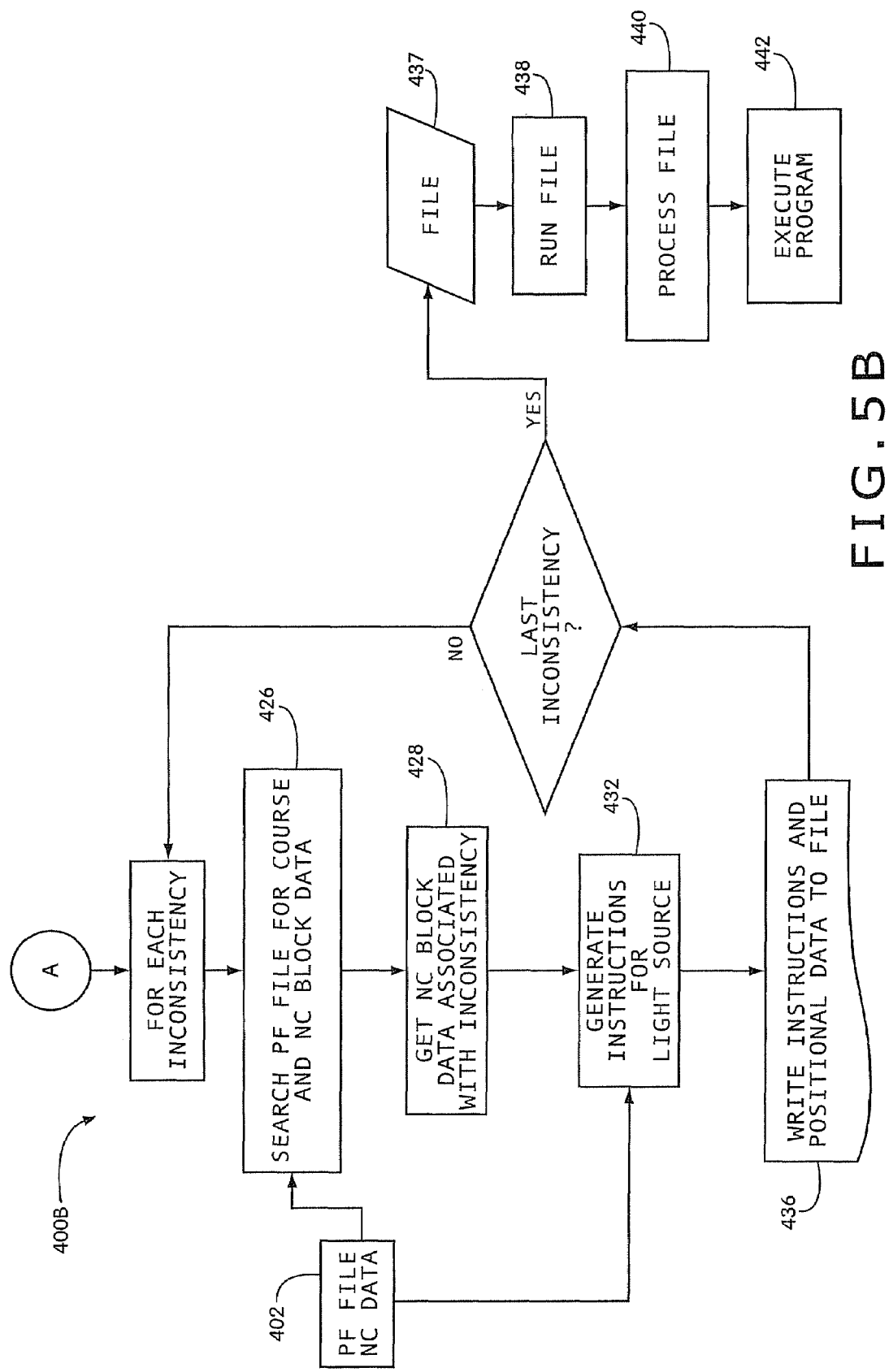

FIGS. 5A and 5B form a process flow diagram illustrating an exemplary method 400 for using light to indicate inconsistency locations on a composite structure. As shown in FIG. 5A, the method may include intelligent front end (IFE) processing of a part fabrication file 402 at operation 404. The part fabrication file 402 can include data and information for a material placement machine to fabricate the composite structure from start to finish. Exemplary information within the file 402 may include numerical control (NC) data defining various approaches and retract motions for the material placement machine and information defining part specifications such as perimeter, size, contour, etc.

FIG. 6 illustrates an exemplary block of numerical control (NC) data 403 that may be included within a part fabrication file 402 for a particular type of material placement machine. FIG. 6 illustrates various lines of data reflecting the material placement machine's location and its operation at a specific point and time. FIG. 6 also illustrates a block 405 of lines associated with an inconsistency location. FIG. 6 is for purposes of illustration only, and the type and content of program code for the material placement machine can vary depending on the particular application and particular material placement machine being used.

Figure 7:
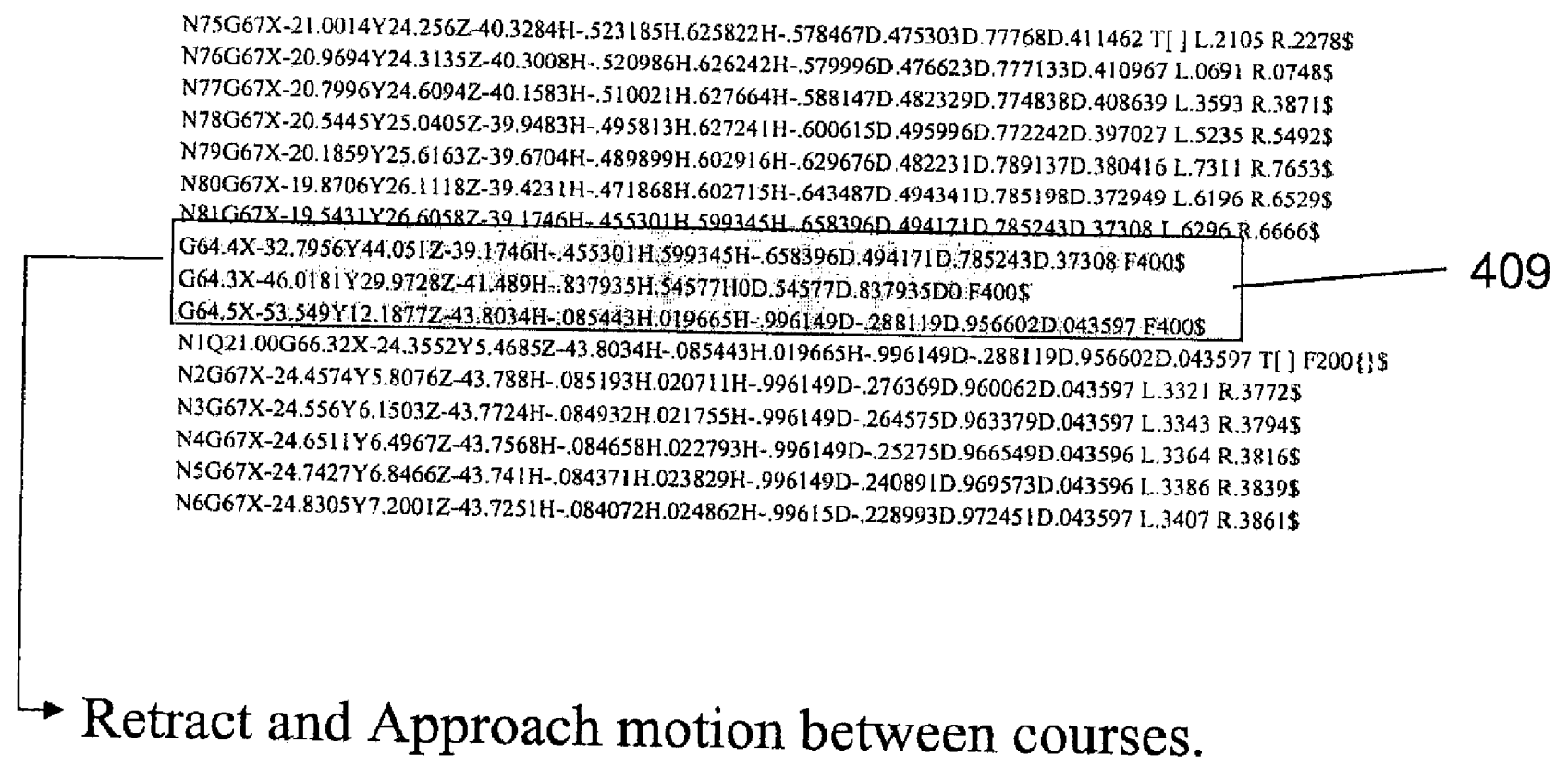

In FIG. 5A, operation 406 includes execution of a program, for example by a processor in communication with the material placement machine. Execution of the program generates instructions or commands for causing the material placement machine to begin placing the material at operation 408. FIG. 7 illustrates an exemplary block of code 409 for generating corresponding retract and approach motions of the material placement machine between courses. FIG. 7 is for purposes of illustration only, and the type and content of the program code for a material placement machine can vary depending on the particular application and particular material placement machine being used.

As shown in FIG. 5A, a ply inspection report is created at operation 412 when the material placement machine completes or comes to the end of a ply or layer, as represented by box 410. The ply, the course, and NC block number associated therewith can be logged or recorded at operation 414.

With reference to FIGS. 5A and 6, current course number and current block number 416 can be sent to an inspection system. Operation 418 (FIG. 5A) includes the inspection system inspecting the composite structure for inconsistencies. Preferably, this inspection occurs generally concurrently with operation 408 in which the material is being placed by the material placement machine. Exemplary systems and methods capable of detecting inconsistencies in a composite structure are described generally below and in more detail in U.S. patent application Ser. Nos. 09/819,922, 10/217,805, 10/628,691, 10/726,099, and/or 10/799,306.

Operation 420 includes determining whether a detected inconsistency is acceptably within certain predefined tolerances or criteria, such as maximum allowable dimensional parameters and tolerances as established by production program. By way of example only, this determination can be made by counting the number of pixels from a digital image representing the inconsistency and then using that pixel count to compute an indirect quantitative measurement for the inconsistency based upon correlation data including a predetermined relationship between pixel count and distance or dimensional limits.

Alternative implementations can also include an operation for determining whether an inconsistency (e.g., an inconsistency determined to be unacceptable at operation 420) can be addressed automatically by the material placement machine without requiring manual intervention by a user. Exemplary inconsistency types that can be addressed by automation are dropped tows and tow gaps having a width equal to the width of a tow. Information about inconsistencies that are determined to be incapable of being adequately addressed by automation can be logged or recorded in the ply inspection report at operation 412. Exemplary inconsistency types which may be determined to be incapable of being addressed by automation with the material placement machine can include foreign objects and debris (FOD) and unacceptable/rejected gaps that are narrower than the width of a tow.

Operation 424 includes determining a location for each inconsistency determined to be outside of pre-defined tolerance, at operation 420. In alternative implementations, operation 424 can include determining a location for each and every inconsistency detected by the inspection system (operation 418). In other implementations, operation 424 can include determining a location for each inconsistency detected by the inspection system (operation 418) determined to be outside of tolerances (operation 420) and also determined to be incapable of being addressed by automation by automation. In yet other implementations, operation 424 can include determining a location for each inconsistency detected by the inspection system (operation 418) and determined to be incapable of being adequately addressed by automation regardless of whether the inconsistency is determined to be acceptable or unacceptable.

In various implementations, inconsistency locations can be determined by exterior monitoring of the material application/lay-down position of the material placement machine. Exemplary systems and methods capable of establishing and retaining generally precise inconsistency locations on the laminate are described generally below and in more detail in U.S. patent application Ser. No. 10/726,099.

The positional data defining inconsistency locations or coordinates can be logged, recorded and tracked at operation 414.

With reference now to FIGS. 5B and 6, operation 426 includes searching the part fabrication file 402 (FIG. 5B) for course and NC block data 405 (FIG. 6) associated with an inconsistency. By way of example, the inspection system upon detection of an inconsistency can produce a signal which is used to flag or identify the numerical control block data defining the coordinates for that inconsistency's location.

At operation 428, the NC block data 405 associated with the inconsistency is obtained or extracted.

Operation 432 includes creating instructions or commands for the light source. Creating these instructions can include accessing the part fabrication file 402. These instructions can automatically cause (e.g., activate, steer, etc.) the light source to direct light at the composite structure to highlight or indicate the location at which an inconsistency is located. Preferably, these instructions for the light source are automatically written based on NC block information and data from the inspection/vision system.

At operation 436, the instructions and positional data (e.g., NC block data 405 extracted at operation 428, commands created at operation 432) can be written to a file 437.

Operations 426 through 436 can be repeated for each inconsistency 20 detected by the inspection system (operation 418, FIG. 5A) determined to be unacceptable (operation 420).

Operation 438 can include running the file 437. Operation 440 can include intelligent front end (IFE) processing of the file 437.

Operation 442 includes execution of the program to cause the light source to direct light at the composite structure to indicate inconsistency locations on the composite structure. This can be accomplished in various ways and with various types of light sources. Exemplary approaches are described above and shown in FIGS. 2 through 4.

Alternative implementations can include using light to indicate each and every inconsistency detected by the inspection system (operation 418, FIG. 5A) in which case operation 420 can be eliminated. Operation 424 can include determining a location for each and every inconsistency detected by the inspection system at operation 418. Operations 426 through 436 can be repeated for each inconsistency detected by the system at operation 418.

Yet other implementations can include using light to indicate only those inconsistencies determined to be unacceptable (operation 420) and also determined to be incapable of being adequately addressed by automation. This latter determination can be made, for example, at an operation between operations 420 and 424. Operation 424 can include determining a location for only those inconsistencies detected by the inspection system (operation 418, FIG. 5A) determined to be unacceptable (operation 420) and also determined to be incapable of being addressed by automation. The number of times that operations 426 through 436 are repeated will depend on the number of such inconsistencies.

Still yet other implementations can include using light to highlight inconsistencies detected by the inspection system (operation 418, FIG. 5A) and determined to be incapable of being adequately addressed by automation without regard for whether such inconsistencies are determined to be unacceptable. Operation 420 can include determining whether a detected inconsistency can be addressed by automation. Operation 424 can include determining a location for each inconsistency detected by the inspection system (operation 418, FIG. 5A) and determined to be not capable of being addressed by automation. The number of times that operations 426 through 436 are repeated will depend on the number of such inconsistencies.

In each of these various implementations, method 400 enables automated generation of program code for automatically causing one or more light sources to direct light at a composite structure to indicate inconsistency locations on the composite structure.

Accordingly, implementations of the disclosure utilize light to make inconsistency locations on a composite structure readily identifiable by an operator. This usage of light to indicate inconsistency locations eliminates the need to apply foreign material (e.g., ink, other marking media, etc.) onto the ply surface, and also enables further reductions in machine down time by eliminating the required maintenance associated with ink-based marking systems to keep ink lines clear, reservoirs filled, and tips primed.

In addition, light-based marking systems can be less complex and more compact than ink-based marking systems wherein one or more suitable light sources can replace numerous ink-based marking components, such as relatively complex hardware, attachment hardware, pumps, reservoirs, solenoids, and applicators.

Using light instead of ink to indicate inconsistency locations also eliminates any concerns about surface contamination of the laminate by the ink (or other marking media) and any potential of such contamination to reduce structural performance of the part. Providing a suitable alternative to ink-based marking systems also eliminates the cost and time normally required to carefully select an appropriate ink that is compatible (won't act as a contaminant) with the composite substrate, has a low enough viscosity to freely flow through supply lines and nozzles, and dries quickly enough to prevent runs on the part surface but dries slowly enough to eliminate clogging.

Figure 8:
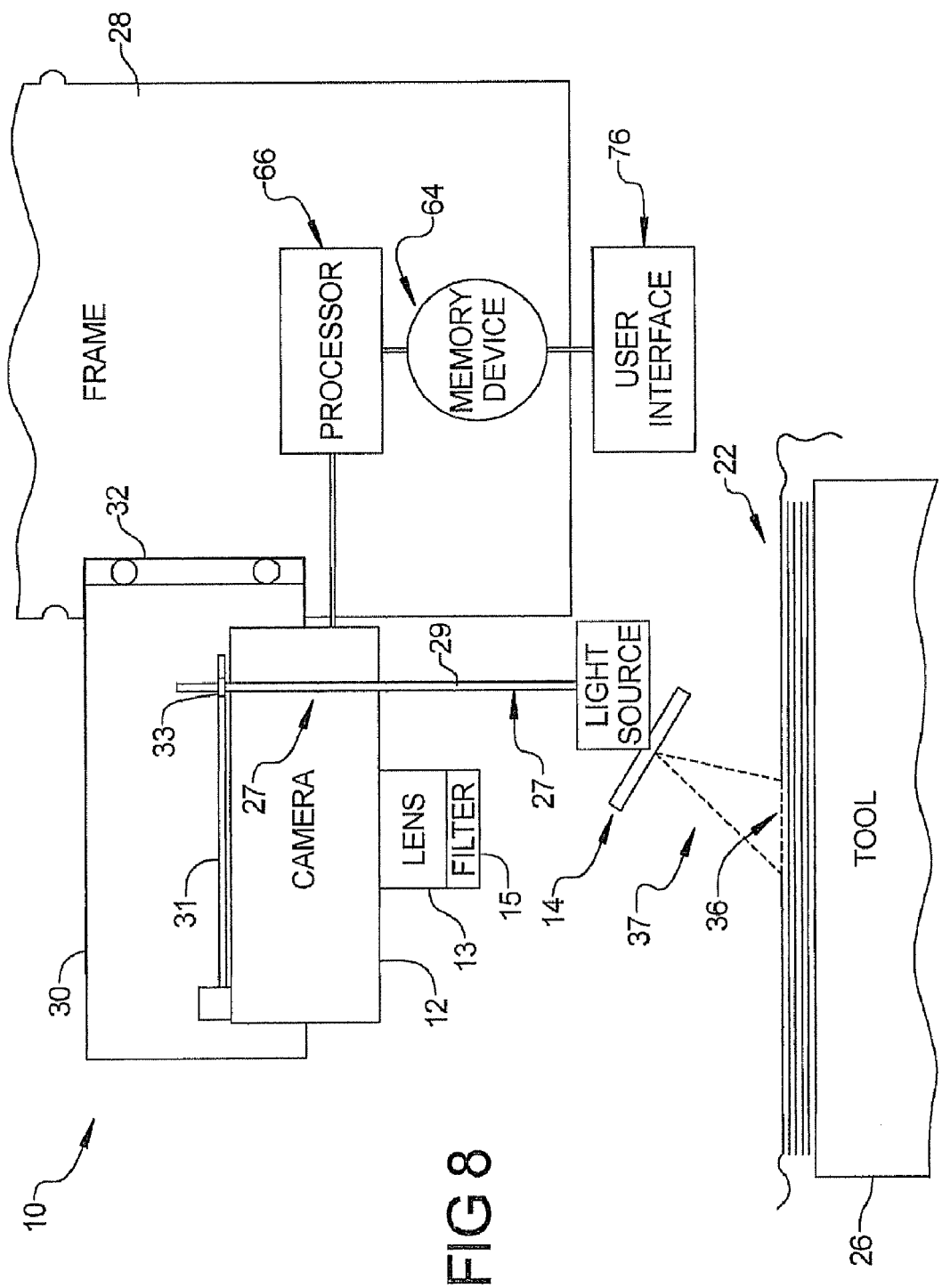
FIG. 8 is a schematic view of an exemplary system for using light to indicate inconsistency locations positioned adjacent an exemplary system for inspecting a composite structure for inconsistencies.
Figure 9:
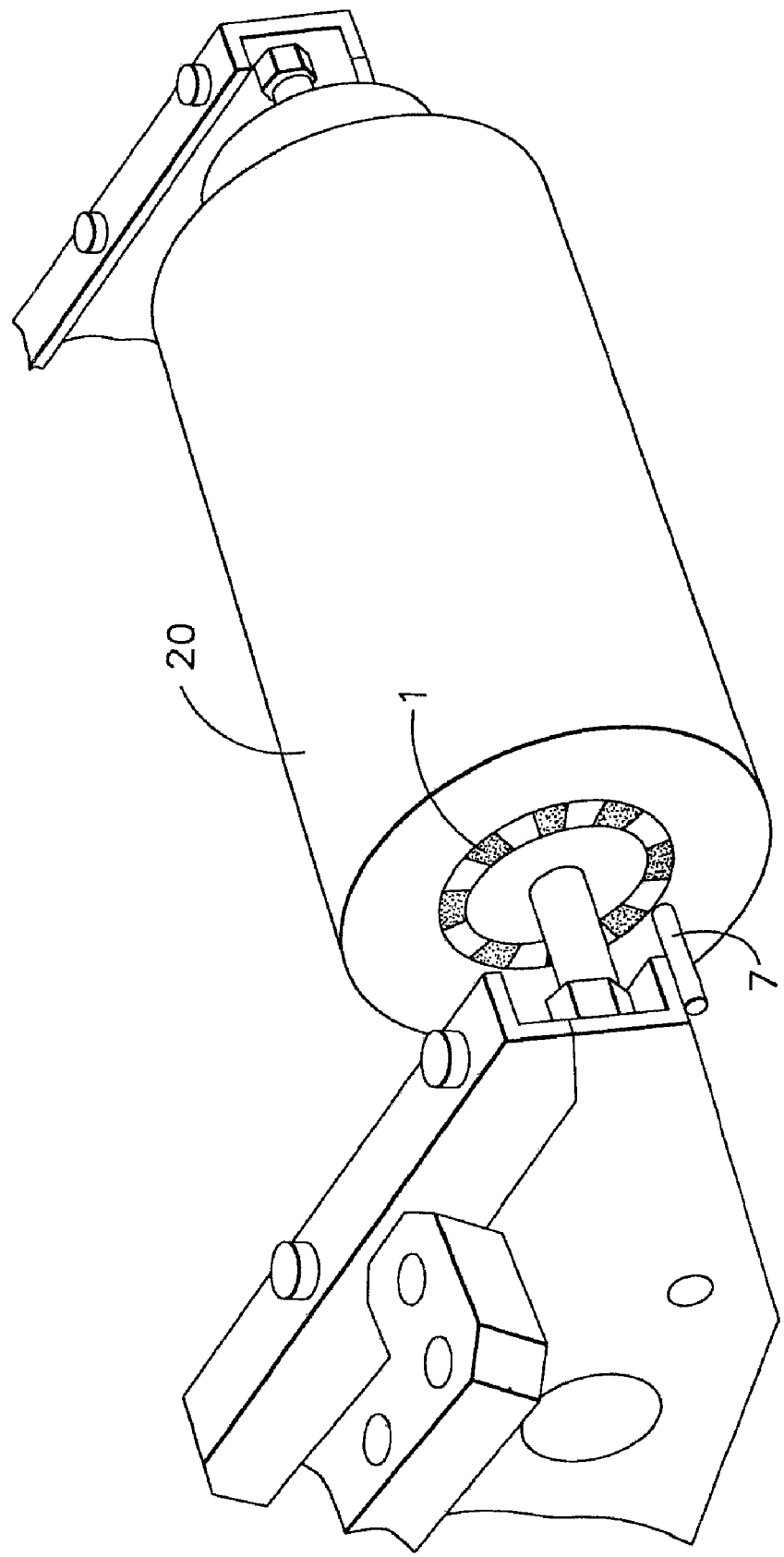
FIG. 9 is a perspective view of an exemplary compaction roller having a code ring coupled thereto for common rotation therewith and a photo sensor positioned to monitor the code ring.

An exemplary system 10 which can be used at operation 416 (FIG. 5A) to detect inconsistencies in a composite structure is illustrated in FIG. 8. It is understood that while various implementations are described herein in conjunction with the system 10, various implementations of the disclosure can also be used with other inspection systems. The following description of the system 10 is merely exemplary in nature and is in no way intended to limit the various implementations of the disclosure, their applications and/or uses.

As shown in FIG. 8, the system 10 includes at least one camera 12 and at least one light source 14. The camera 12 is connected to a processor 66 for interpreting the images the camera 12 captures, or to a storage device 64 for storing the images, or both, as discussed more fully below.

The system 10 may also include a user interface 76 that is in communication with the processor 66. The user interface can be programmed such that it can run from a wide range of software applications, including but not limited to DOS, Windows 98, Windows/NT, Windows 2000, Windows CE, Linux, Unix, and equivalents. The user interface 76 can include a display screen, such as on a computer monitor, and can also include an input device, such as a keyboard and mouse (not shown), for permitting an operator to move a cursor about the display screen and input various system settings and parameters. The display screen can also be touch-sensitive for permitting the operator to input the desired settings by manually touching regions of the display screen. The user interface 76 can includes a window in which an image The light source 14 is positioned to emit light for illuminating the composite structure 22. The illumination is reflected differently by inconsistencies in the composite structure than from portions of the composite structure that are inconsistency free. For example, illumination reflecting off non-inconsistency portions of the composite structure 22, and light that fails to reflect off of inconsistencies in the composite structure 22, or vice versa, creates visible images that can be captured by the camera 12. Details regarding systems and methods for identifying inconsistencies in a composite structure during fabrication thereof are included in previously referred to U.S. patent application Ser. Nos. 09/819,922, 10/217,805, 10/628,691, 10/726,099, and 10/799,306.

Figure 10:
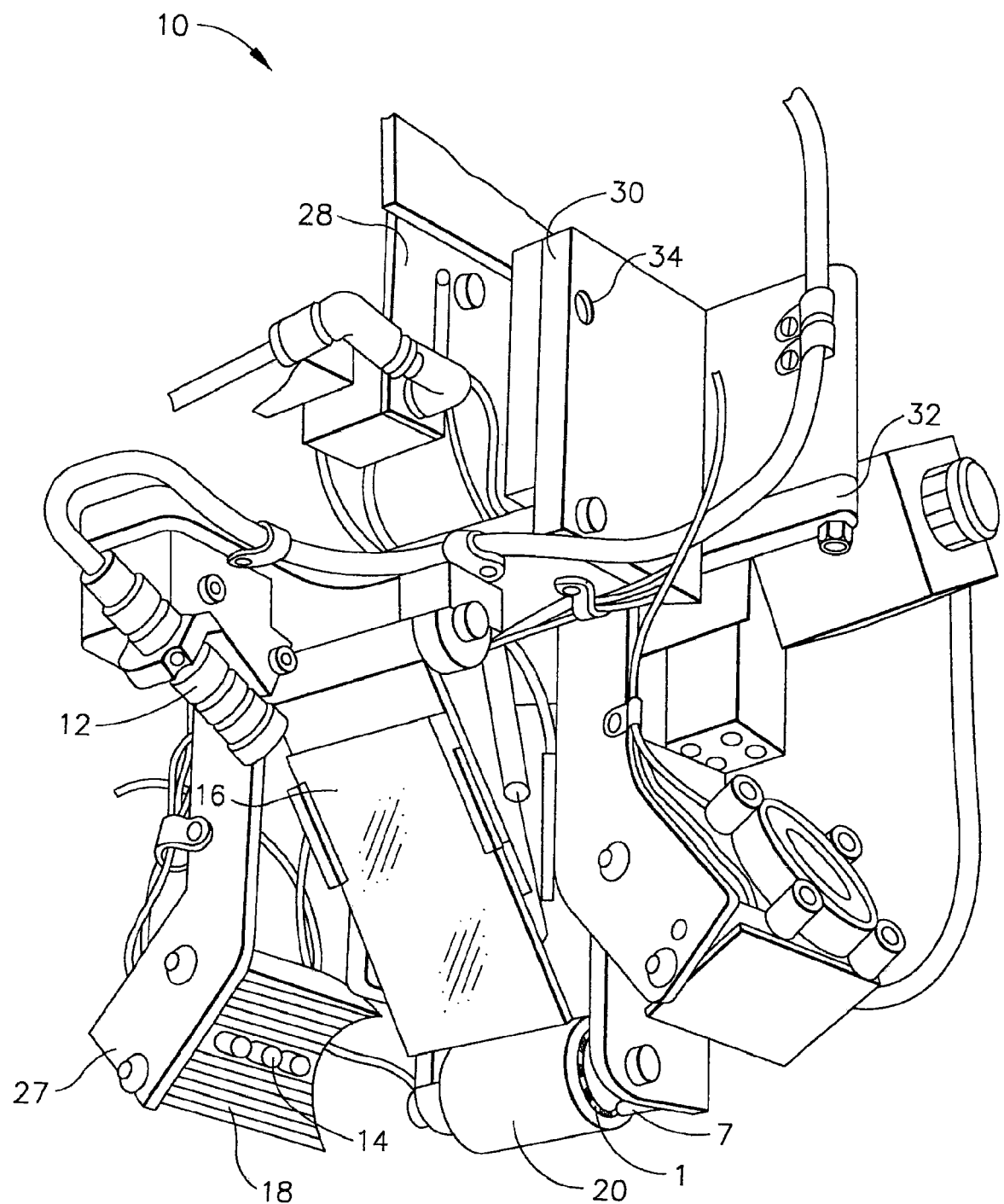
FIG. 10 is a perspective view of another exemplary system for inspecting a composite structure for inconsistencies.

As shown in FIG. 8, the camera 12 is positioned near the composite structure 22 so as to capture images of portion of the composite structure being illuminated, which is typically immediately downstream of the nip point at which a composite tow is joined with the underlying structure. Alternatively, and as shown in FIG. 10, a reflective surface 16 may be positioned near the composite structure (the composite structure is not shown in FIG. 10), and angled such that the reflective surface 16 reflects an image of the illuminated portion of the composite structure. The camera 12 may be positioned to point toward the reflective surface 16 in order to capture close-range images of the illuminated portion of the composite structure from the reflective surface 16. More than one reflective surface 16 may also be utilized in further embodiments of the disclosure in which the reflective surfaces 16 cooperate in order to direct images of the illuminated portion of the composite structure to the camera 12.

A wide range of cameras can be used including commercially-available cameras capable of acquiring black and white images. In one embodiment, the camera 12 is a television or other type of video camera having an image sensor (not shown) and a lens 13 (FIG. 8) through which light passes when the camera 12 is in operation. Other types of cameras or image sensors can also be used, such as an infrared-sensitive camera, a visible light camera with infrared-pass filtration, a fiber optic camera, a coaxial camera, Charge Coupled Device (CCD), or Complementary Metal Oxide Sensor (CMOS).

The camera 12 can be positioned proximate the composite structure 22 on a stand (not shown) or mounted to a frame 28 or similar device.

In those embodiments that do not include a reflective surface 16, the camera 12 may be mounted to the frame 28 by way of a bracket 30 and associated connectors 32, as shown in FIG. 8. The connectors 32 may be rivets, screws or the like that mount the camera 12 to the frame 28 in a stationary position. Alternatively, the connectors 32 may be a hinge-type connector that permits the camera 12, light source 14, and associated assembly to be rotated away from the composite structure 22. This embodiment is advantageous in situations where other parts of the material placement device, particularly the parts located behind the camera 12 and associated assembly, must be accessed, such as for maintenance, cleaning, or the like.

FIG. 10 illustrates an alternative embodiment of the hinge-type connector 32 that mounts the camera 12, reflective surface 16, light source 14, and associated assembly (e.g., camera assembly) to the frame 28 by way of a bracket 30. A suitable fastener, such as a thumbscrew or any other fastener that may be removed or loosened with relative ease, can be inserted through hole 34 and then tightened to secure the camera assembly in place for operation. The fastener may be loosened or removed, for example, to rotate the camera assembly away from the compaction roller 20 and other parts of the fiber placement device.

With further reference to FIG. 8, a filter 15 can be placed on the lens 13 for filtering light in a particular manner. In one embodiment, the filter 15 is designed to filter light such that only the infrared component or a certain infrared wavelength or range of wavelengths of light can pass into the camera 12. In this manner, the filter 15 prevents ambient visible light from entering the camera 12 and altering the appearance of the captured image.

Other methods of filtering light can also be used to achieve the same, or at least similar, result. For example, the camera may be designed to include a built-in filter of equivalent optical characteristics. In addition, the filter can be located between the camera lens 13 and image sensor. Alternatively, the camera may include an image sensor that is only sensitive in the infrared spectrum (e.g., an infrared-sensitive camera), thus eliminating the need for the filter.

The light source 14 of the system 10 will now be described in more detail. The light source 14 is positioned to emit light for illuminating at least a portion of the composite structure 22.

In FIG. 8, the light source 14 is shown positioned at an oblique angle 37 relative to the composite structure 22. The oblique angle 37 may be about forty-five degrees, although other angles are possible depending on the application. In addition, the light source 14 is also shown positioned to emit light in a direction substantially perpendicular to the direction of placement of the strips 24 in order to highlight the inconsistencies 36, as described below.

Figure 12:
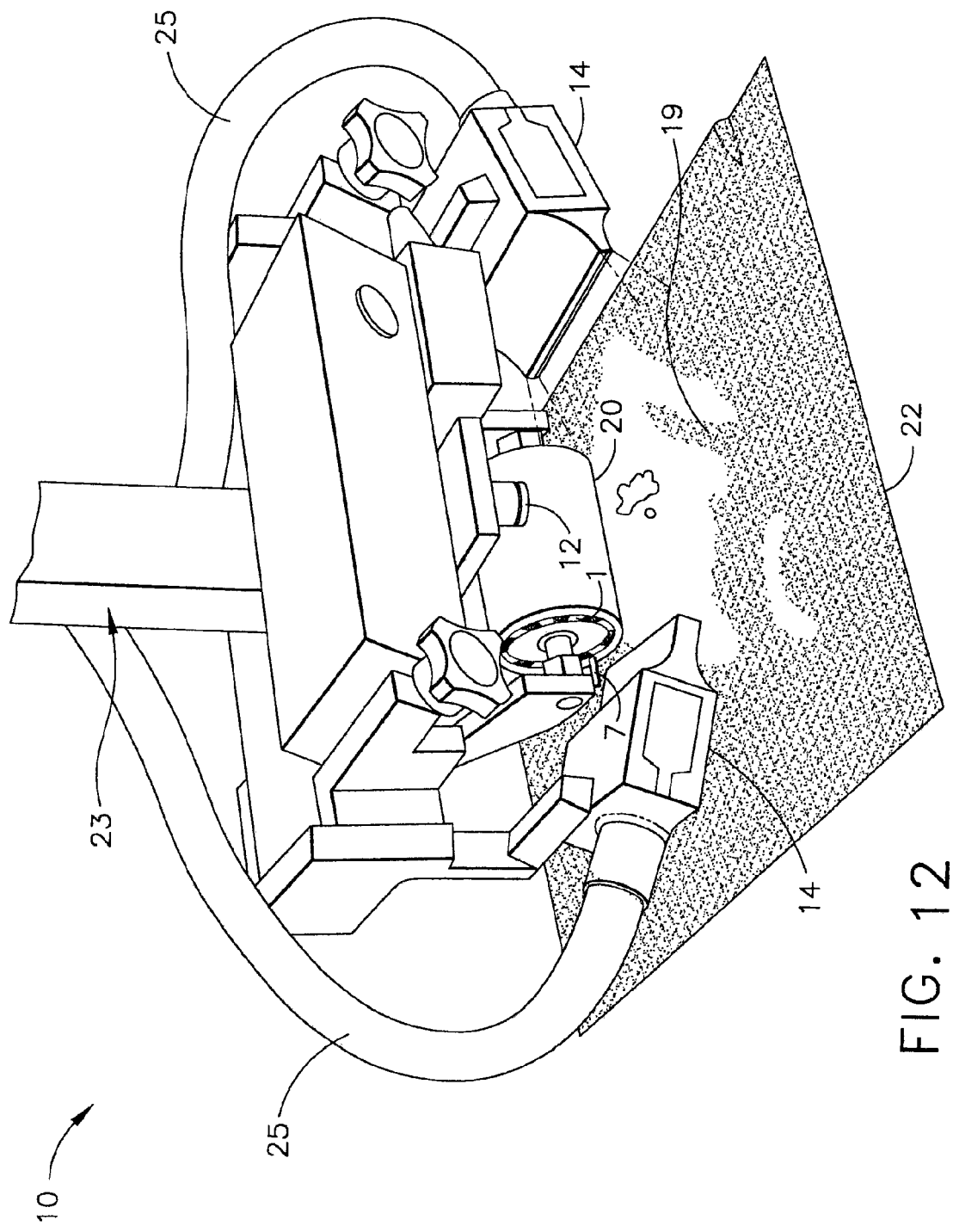
FIG. 12 is a perspective view of another exemplary system for inspecting a composite structure for inconsistencies.

Further, the system 10 may include more than one light source. For example, the embodiment of FIG. 10 includes two light sources 14 positioned relative to the composite structure and compaction roller 20 on either side of the reflective surface 16 and camera 12. Another exemplary embodiment that includes two light sources 14 is shown in FIG. 12 in which two linear optical fiber arrays are positioned on opposed sides of the camera 12.

In FIG. 8, the light source 14 is adjustably positioned relative to the composite structure 22 by mounting or attaching the light source 14 to a mounting apparatus 27. The mounting apparatus 27 can include a main shaft 29, a secondary shaft 31, and a locking clamp 33 for quickly and accurately adjusting the position of the light source 14. The mounting apparatus 27, in turn, can be attached to the frame 28, to the camera 12, to the bracket 30, or to some other object that defines a common position for both the light source 14 and the camera 12 such that the light source 14 and camera 12 maintain a constant spatial relationship relative to one another.

The quality and magnitude of the surface illumination of the composite structure can be affected by ambient lighting and by reflectivity of the material. Accordingly, embodiments of the disclosure advantageously employ an infrared light source to more effectively illuminate dark inconsistencies on a dark background. In this regard, the light source 14 can be selected from an infrared light or another type of light having an infrared component, such as a halogen light source (FIG. 11) or other incandescent light sources (not shown). In other embodiments, the light source 14 can also include a fluorescent light source (e.g., white light LEDs, low pressure/mercury filled phosphor glass tube, etc.), a strobe or stroboscopic light source, a noble gas arc lamp (e.g., xenon arc, etc.), metal arc lamp (e.g., metal halide, etc.) and a lasers (e.g., pulsed lasers, solid state laser diode arrays, infrared diode laser arrays, etc.). The light from the light source 14 may also be pumped from through optical fibers to the point of delivery, such as is shown in FIG. 12.

In some embodiments, the light source 14 is operated at a power level that maximizes, or at least significantly increases, the infrared (IR) component of the light which works well for inspecting dark tow material, such as carbon. In this regard, exemplary power levels in the range of up to about one hundred fifty watts (150 W) in the wavelength range of about seven hundred nanometers to eleven hundred nanometers (700 nm-1100 nm) have been sufficient. However, the particular power levels and wavelengths for the light source will likely depend, at least in part, on the camera's speed and sensitivity, speed at which the material is being laid, delivery losses, and reflectivity of the material being inspected, among other factors. For example, in other embodiments, wavelengths and power levels suitable for inspecting highly reflective materials can be employed.

In the embodiment shown in FIG. 8, the light source 14 may comprise a plurality of LEDs arranged in an array or cluster formation. In one specific embodiment, the light source 14 includes 24 LEDs mounted in an array upon a three-inch square printed circuit board.

Figure 11:
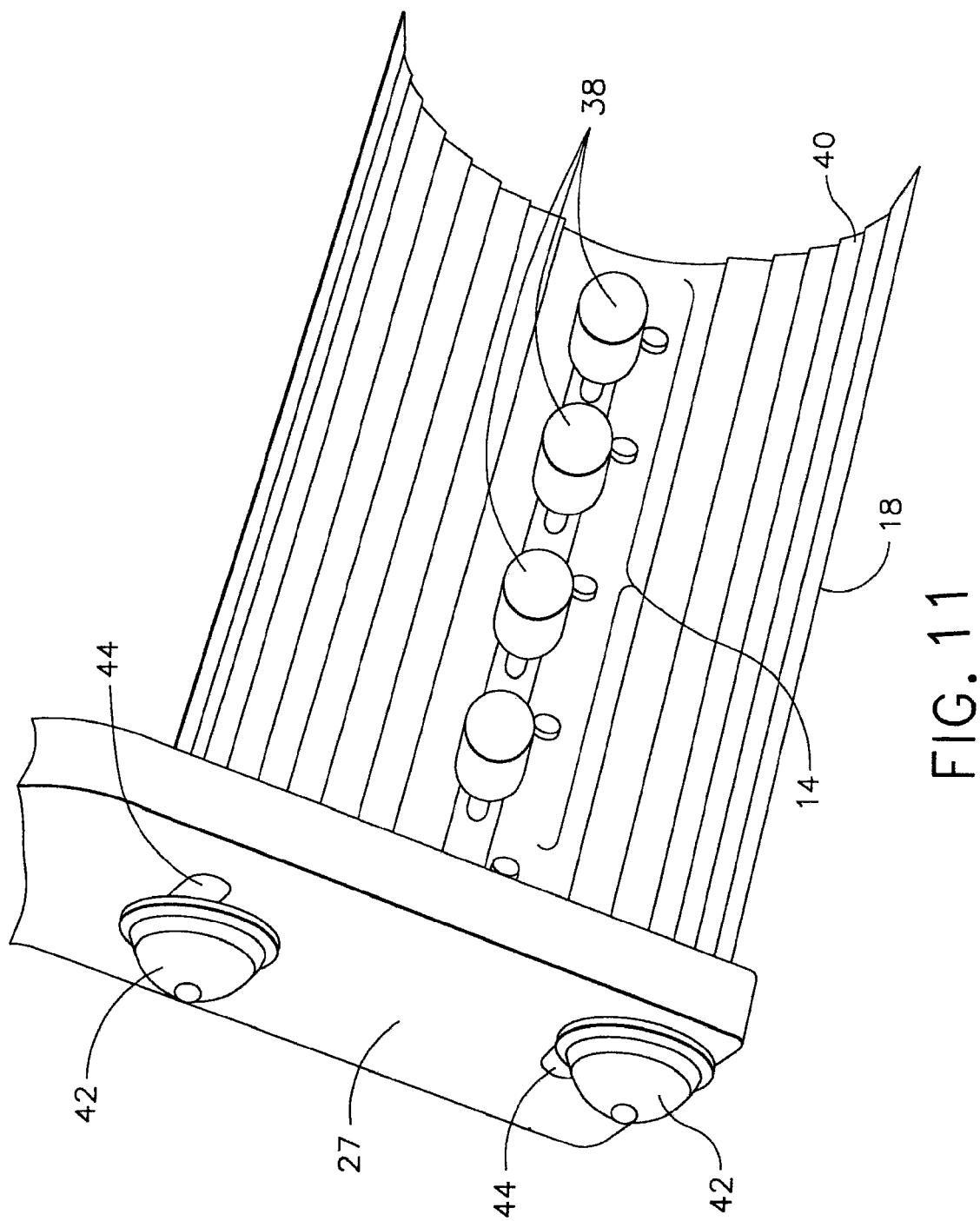
FIG. 11 is a perspective view of a light source according to the system embodiment shown in FIG. 10.

In another embodiment shown in FIGS. 10 and 11, the light source 14 includes four halogen light bulbs 38, although other quantities can and have also been used.

Figure 13:
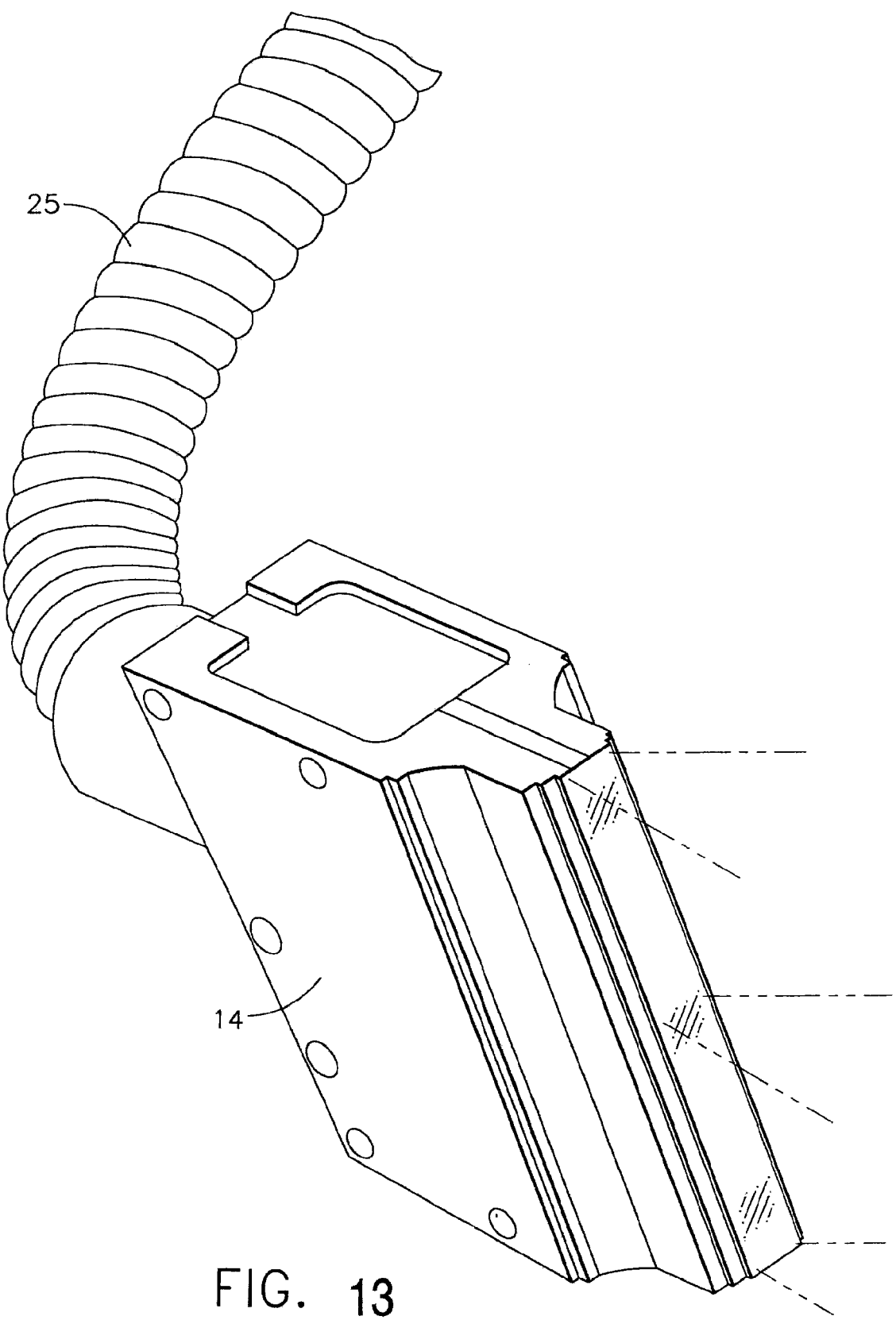
FIG. 13 is a perspective view of a light source according to the system embodiment shown in FIG. 12.
Figure 14:
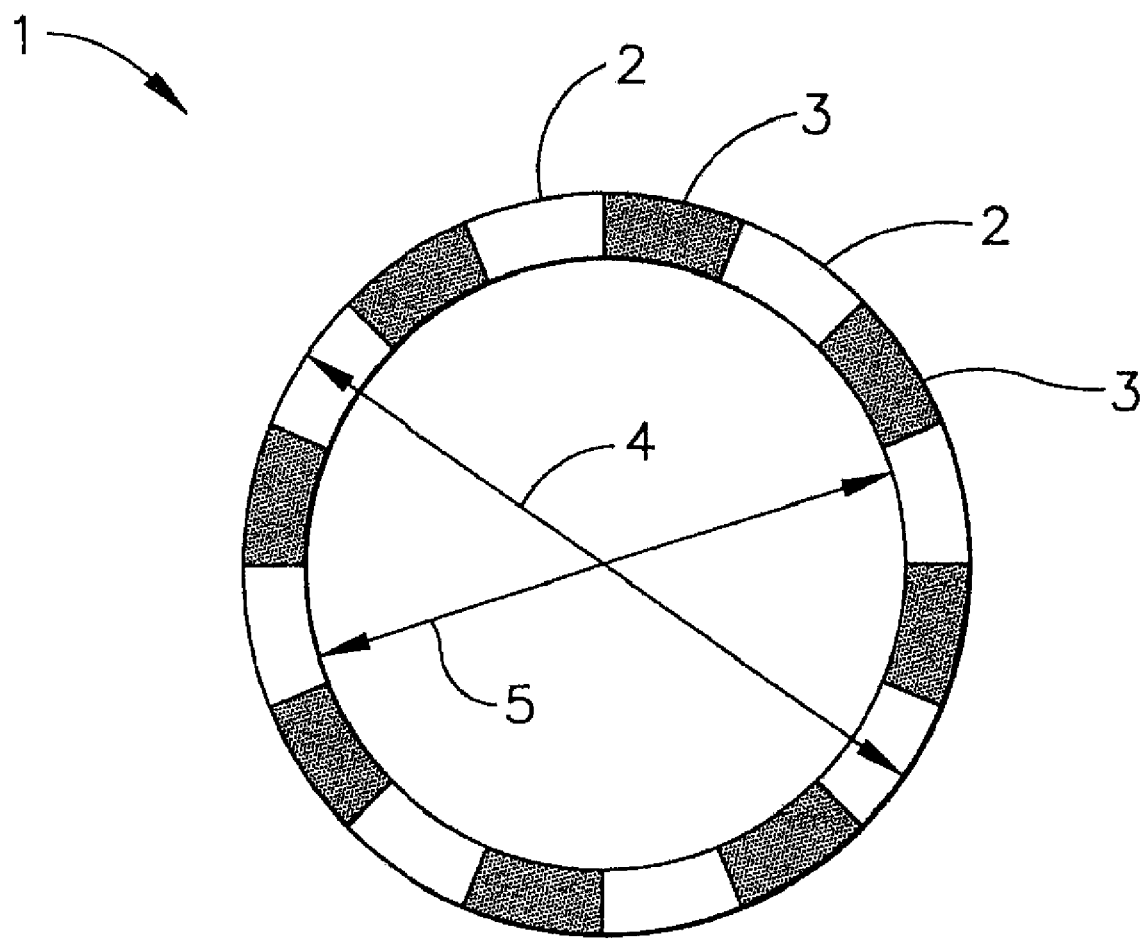
FIG. 14 is a schematic view of the code ring shown in FIG. 9.

In the embodiment shown in FIG. 12, the light source 14 includes two linear optical fiber arrays positioned on opposite sides of the camera 12. The arrays emit light supplied from a remote source (not shown) through an optical fiber bundle 25. An illuminated linear array 14 is shown in FIG. 13.

Referring back to FIG. 10, the system 10 may further include a light reflection element 18 located near the light source 14. The reflection element 18 includes a series of light reflecting surfaces 40 (FIG. 11) that redirect the light towards the desired area to be illuminated. This levels the illumination across the surface and eliminates, or at least substantially reduces, areas of intense light (i.e., hotspots) created by the brightest portion of the light source 14. Hotspots are undesirable because hotspots can prevent consistent illumination of the composite structure, which may lead to errors during the processing of the images captured by the camera 12.

The light reflection elements 40 are particularly advantageous for illuminating curved/contoured surfaces of composite structures because the redirection of the light permits a larger portion of the composite structure to be evenly illuminated.

As shown in FIG. 11, the reflection element 18 is curved around the light source 14, such as in a parabolic shape. On the surface of the reflection element 18 that faces the light source 14, the reflection element 18 includes curved steps 40 substantially parallel to the light source 14. The distance between and curvature of the steps 40 can be chosen to be sufficient to provide even illumination from the sum of the two light sources, one on either side of the region of interest. This enables the reflection element 18 to provide more consistent illumination of the composite structure 22, which prevents, or at least reduces, image processing errors due to inconsistent illumination of the composite structure 22. Alternatively, the shape and/or surface configuration of the reflection element 18 can be modified in other ways that also produce consistent illumination and scattering of the light produced by the light source 14 over the desired portion of the composite structure 22.

In an exemplary embodiment, the reflection element 18 has an overall parabolic shape with seventeen parabolic curved steps 40 having a range of widths from about 0.125 inches at the outer edge of the reflection element 18 to about 0.250 inches at the center of the reflection element 18. The reflection element 18 also has a uniform step height of about 0.116 inches. In other embodiments, however, the reflection element may be provided with different numbers of steps having different uniform or varying widths and different uniform or varying step heights.

Furthermore, the reflection element 18 may be adjusted in order to direct the light produced by the light source 14 and scattered by the reflection element 18 toward the desired portion of the composite structure. For example, as shown in FIG. 11, the reflection element 18 is adjustably mounted to the mounting apparatus 27 with fasteners 42. The loosened fasteners 42 can move within slots 44 to correspondingly adjust the angle of the reflection element 18 relative to the composite structure. Once the reflection element 18 is positioned appropriately, the fasteners 42 are tightened to secure the reflection element 18 in the desired position. Adjustments of the reflection element 18 can also be enabled by other methods, such as by electronic means that permit remote adjustment of the reflection element 18.

It has been observed that the composite structure 22 can produce high glare when illuminated across the direction of placement of the strips 24 but produces substantially less glare when illuminated along the direction of placement of the strips 24. The systems and methods of at least some embodiments exploit the high-glare/low-glare phenomenon by casting light across the top layer of the composite strips 24 in a direction substantially perpendicular to the direction of placement of the strips 24. This produces a relatively large amount of glare on the top layer of the composite structure 22. The underlying layers, which produce significantly less glare than the top layer because of their orientation, will show through any gaps or other inconsistencies in the top layer and thus be easily located. In addition, twists and other surface inconsistencies in the top layer will alter the orientation of the strips in the top layer and thus correspondingly alter, i.e., decrease, the glare of the top layer at the inconsistency location.

While the high-glare/low-glare phenomenon can occur when illuminated with either visible light or infrared light, the filter 15 used in one embodiment of the system 10 substantially removes the glare caused by ambient light such that only the glare caused by the infrared light source is used to locate the inconsistencies. Accordingly, the filter 15 removes the interference of ambient light as the composite structure 22 is being examined for inconsistencies.

In any of the system embodiments described herein, there may be one or more cameras 12 and/or one or more light sources 14 with or without reflection elements 18 (collectively referred to as light sources, hereinafter). In addition, the one or more cameras 12 and/or the one or more light sources 14 may be moveable relative to the composite structure. The multiple cameras 12 and/or multiple light sources 14 and the moveability of the camera(s) 12 and/or the light source(s) provides system 10 flexibility in order to capture the most accurate images of the composite structure. Multiple and/or moveable light source(s) 14 permit consistent and sufficient illumination of the desired portion of the composite structure, regardless of the shape of the composite structure. Likewise, multiple and/or moveable camera(s) 12 enable capturing an accurate image of any area of the composite structure, regardless of the shape of the composite structure. As such, the multiple and/or moveable light source(s) and/or camera(s) are particularly advantageous when illuminating and capturing images of curved/contoured portions of composite structures. The multiple and/or moveable light source(s) and/or camera(s) are also advantageous in illuminating and capturing images of composite strips having a width that makes it difficult to illuminate and/or capture images of the entire strip, such that the position of the light source(s) and/or camera(s) may be moved over the entire strip, and/or multiple stationary light source(s) and/or camera(s) may be positioned to cover the entire strip. Systems including moveable cameras and light sources are described in detail in previously referred to U.S. patent application Ser. No. 10/217,805.

The camera 12 and/or the reflective surface 16, which along with the light source 14 and any reflection element 18, can be mounted to the head unit to allow the camera 12 to continuously capture real-time images of the composite structure 22 and the strips 24 as the head unit moves across the composite structure 22 and the composite strips 24 are laid down. If the composite structure 22 is not planar, the inspection point should preferably be as close to the nip point as possible, as described above. If the composite structure 22 is planar, the inspection point can be located further from the placement head unit. In either case, the images can be stored in a memory device 64 for future analysis and/or processed immediately by the processor 66.

The processor 66 may receive the images from the camera 12 or from the memory device 64 in which images have been stored. The processor 66 may then process and analyze the images to facilitate the reliable detection of inconsistencies. In at least one embodiment, the processor 66 and memory device 64 are components of a conventional computer.

Various methods can be used to determine the inconsistency locations (e.g., linear distance 19 and lateral distance 21 to an inconsistency 36, FIG. 1) at operation 424 (FIG. 5A). Details regarding systems and methods for determining inconsistency locations are included in previously referred to U.S. patent application Ser. No. 10/726,099.

In an exemplary implementation, linear distance to an inconsistency-along a course can be determined by multiplying the velocity of the material placement head unit along the course with the amount of time that has lapsed between when the course began and when the inconsistency is detected.

The start and stop of a course can be determined using signals from the machine load cell which indicate whether or not pressure is being applied to the compaction roller 20 (FIGS. 7, 8, and 10). Receipt of a "pressure on" signal from the machine load cell indicates that the compaction roller 20 is in contact with the composite structure 22 and therefore, that a course has been started. Receipt of a "pressure off" signal indicates that the compaction roller 20 is no longer in contact with the composite structure 22, and therefore that a course has been completed. Accordingly, the time between course start and inconsistency detection can be determined by tracking the amount of time elapsing between receipt of the "pressure on" signal from the machine load cell and the receipt of the signal indicating detection of an inconsistency.

Alternatively, course start and stop can be determined by receipt of a signal from a device employing proximity sensors, lasers, or sound detectors positioned for determining whether or not the compaction roller 20 is in contact with the composite structure 22.

In one implementation, velocity of the head unit is determined by determining the angular velocity of the compaction roller 20 and multiplying the angular velocity by a circumference of the compaction roller 20. Alternatively, other methods can also be used to determine the velocity of the head unit, such as by using a radar gun commonly used for law enforcement purposes in monitoring vehicular speeds along roadways.

Referring to FIGS. 7, 8, and 12, the angular velocity of the compaction roller 20 can be determined by a code ring 1 coupled for common rotation with the compaction roller 20. As shown, the code ring 1 includes alternating contrasting portions 2 and 3, such as alternating black and white segments. In FIG. 12, the code ring 1 includes an outer diameter 4 of about 1.010 inches and an inner diameter 5 of about 0.844 inches, although other ring sizes can also be employed. In other embodiments, the contrasting portions can be provided directly on the compaction roller 20 (e.g., marked on, painted on, etc.), thereby eliminating the need for the separate code ring 1.

With further reference to FIGS. 7 and 8, a photo sensor 7 (e.g., an off-the-shelf photo diode, etc.) is positioned to monitor and capture real-time images of the light-to-dark transitions of the code ring 1 as the code ring 1 rotates along with the compaction roller 20. By detecting and counting the light-to-dark transitions of the ring 1, the compaction roller revolutions can be counted and monitored. The frequency at which the light-to-dark transitions occur can be used to establish the angular velocity of the compaction roller 20. Preferably, axial motion in the compaction roller 20 is minimized in order to maintain the distance from the photo sensor 7 to the code ring 1 constant, which, in turn, allows for more accurate determination of the machine head unit's velocity.

In another exemplary embodiment, the linear distance to an inconsistency along a course can be determined by counting the number (whole and fractional) of revolutions the compaction roller 20 makes from the start of the course to the inconsistency and multiplying that number of revolutions by the circumference of the compaction roller 20. By way of example, the photo sensor 7 and code ring 1 can be used to count the number of revolutions of the compaction roller 20 between receipt of the "pressure on" signal from the machine load cell and receipt of the signal indicating that an inconsistency has been detected.

Various methods can also be employed to determine the lateral distances to inconsistencies from the first end 11 of the composite structure 22. See FIG. 1. In one exemplary embodiment, lateral distance to an inconsistency can be calculated by counting the total number of completed courses, not including the course in which the inconsistency resides, and then multiplying the average width of a course by the number of completed courses. This method is particularly effective for tape placement in which each course is the same width, i.e., the width of the tape.

The total number of completed courses can be determined by tracking or counting receipt of the pressure on/off signals from the machine load cell. Receipt of a "pressure on" signal from the machine load cell indicates that the compaction roller 20 is in contact with the composite structure 22 and has thus started a course. Receipt of a "pressure off" signal indicates that the compaction roller 20 is no longer in contact with the composite structure 22 and has thus completed the course.

For fiber placement courses in which the width of each course may not be equal, the lateral distances to inconsistencies can be accurately determined by employing a "software ruler." More specifically, the lateral distance can be determined by acquiring a digital image of at least the portion of the composite structure including the lateral distance; selecting a pixel set from the digital image that represents the lateral distance; counting the number of pixels comprising the pixel set; and correlating the pixel count with correlation data (e.g., a predetermined relationship between pixel count and distance) to compute an indirect quantitative measurement for the lateral distance.

Figure 16:
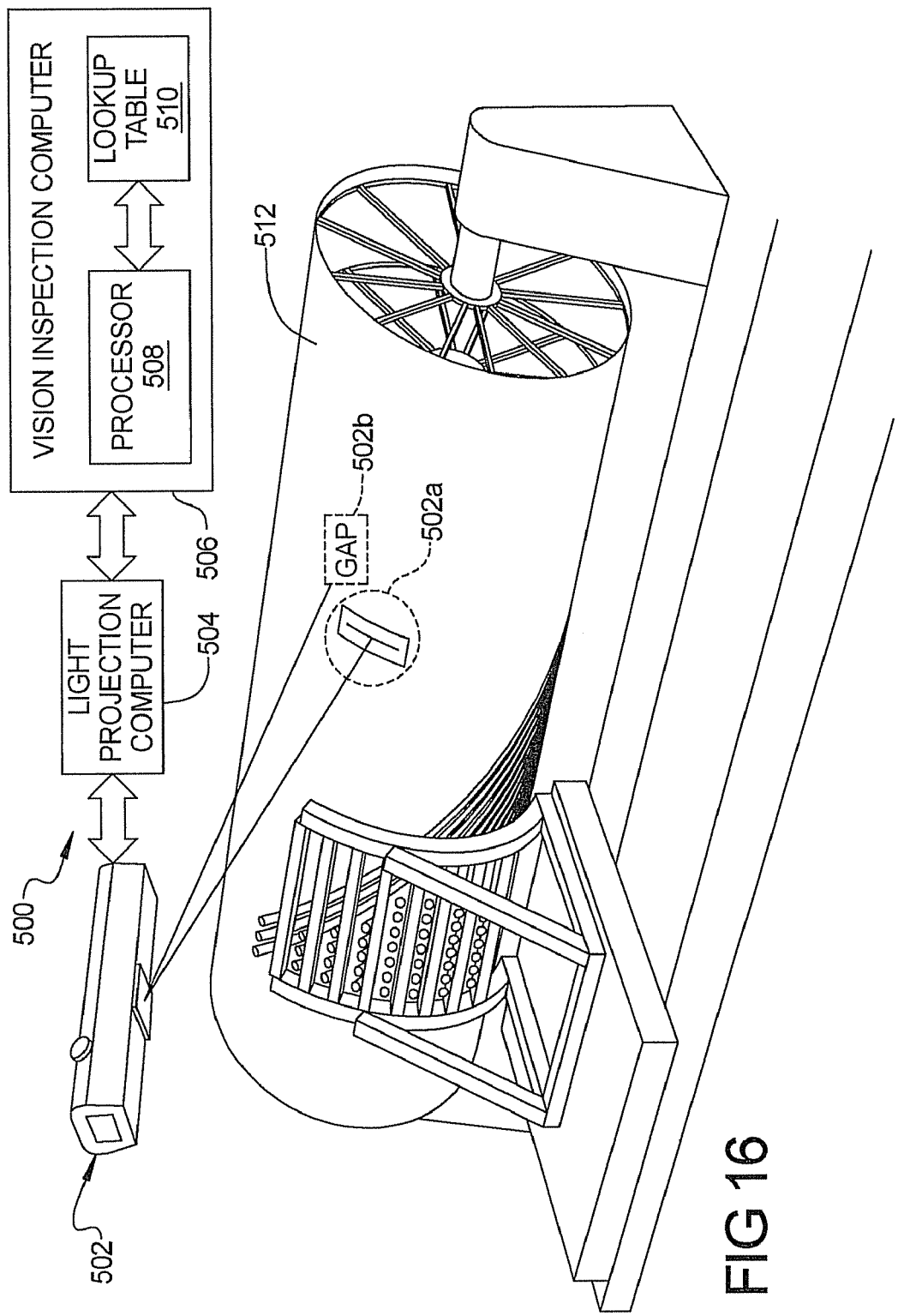
FIG. 16 is a perspective view of another embodiment of the present disclosure that makes use of a lookup table that can be used by a light source system to obtain information on a specific type of detected inconsistency, and to project an optical signal onto a composite structure indicating the specific type of inconsistency existing at a specific location on the structure.

Referring to FIG. 16, an inspection system 500 in accordance with another embodiment of the present disclosure is illustrated. The system 500 makes use of a light source 502 that may be similar or identical to previously discussed light sources, for example one or more lasers, that is/are controlled by a light projection computer 504. A vision inspection computer 506 is in communication with the light projection computer 504. The vision inspection computer 506 includes a processor 508 that is in communication with a lookup table 510. The lookup table 510 may comprise a single lookup table or a plurality of independent lookup tables that are interlinked or otherwise selectively accessible by the processor 508. The following discussion will assume that a single lookup table is being used.

Figure 17:
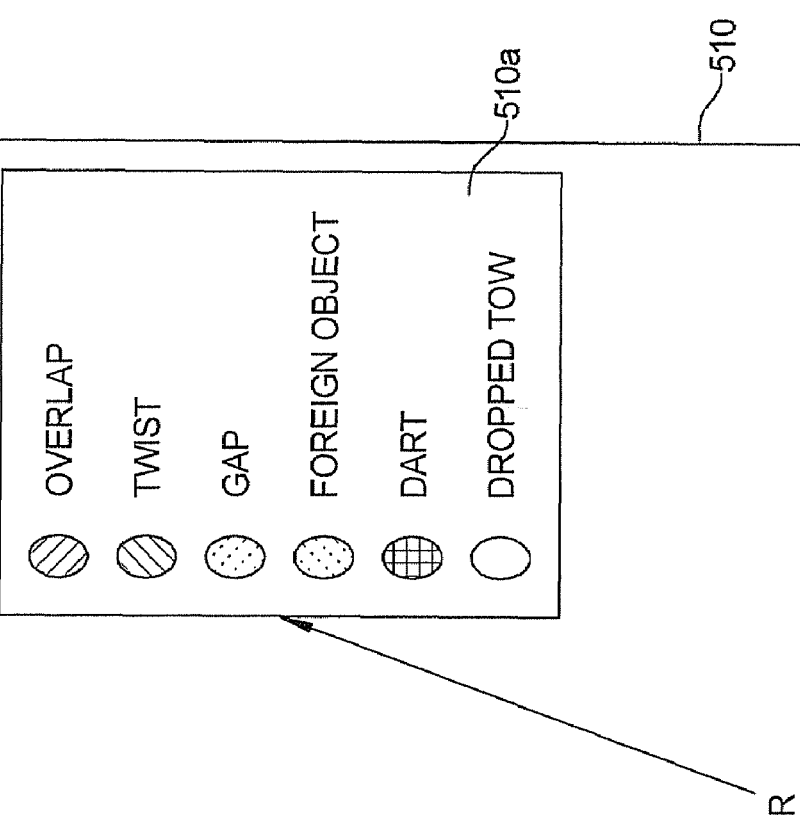
FIG. 17 is a simplified illustration of one exemplary lookup table that may be used with the vision inspection computer of FIG. 16.

With brief reference to FIG. 17, the lookup table 510 may include an inconsistency file 510a. The inconsistency file 510a may include information on a plurality of different identification words, indicia or symbols that are associated with different types of inconsistencies. Several specific types of inconsistencies such as "Overlap", "Twist", "Gap", "Foreign Object", "Dart" and "Dropped Tow" are shown merely for exemplary purposes. Virtually any type of inconsistency could be noted in the inconsistency file 510a. This information is obtained by the processor 508 of the vision inspection computer 506 and provided to the light projection computer 504.

In FIG. 16, the light source projection computer 504 uses the information from the vision inspection computer 506 to generate suitable drive signals to the light source 502. The light source 502 uses the drive signals to generate optical signals 502a and 502b that are directed at the composite structure 512 to illuminate the inconsistency, as well as to project a word, indicia, graphic or symbol onto the composite structure adjacent to the inconsistency that indicates the specific type of inconsistency that is present. In this example a first optical signal portion illuminates an inconsistency 502a while a second optical signal portion provides a symbol, text, indicia or graphic 502b to indicate the specific type of inconsistency present. The optical signal portions from the light source 502 may be produced, for example, by a single laser having a suitable beam splitter for producing two or more optical beams that may be aimed independently. Preferably the optical signal portion providing the specific type of inconsistency is directed at a location closely adjacent the location of the inconsistency, but this is not necessary. Alternatively, a plurality of lasers or other suitable forms of light generating subsystems may be used in the light source 502 to generate the plurality of distinct optical beams. It will be appreciated that a different subsystem (not shown) may be employed to physically aim the optical beam(s) from the light source 502 onto the inconsistency and/or its adjacent area.

Figure 18:
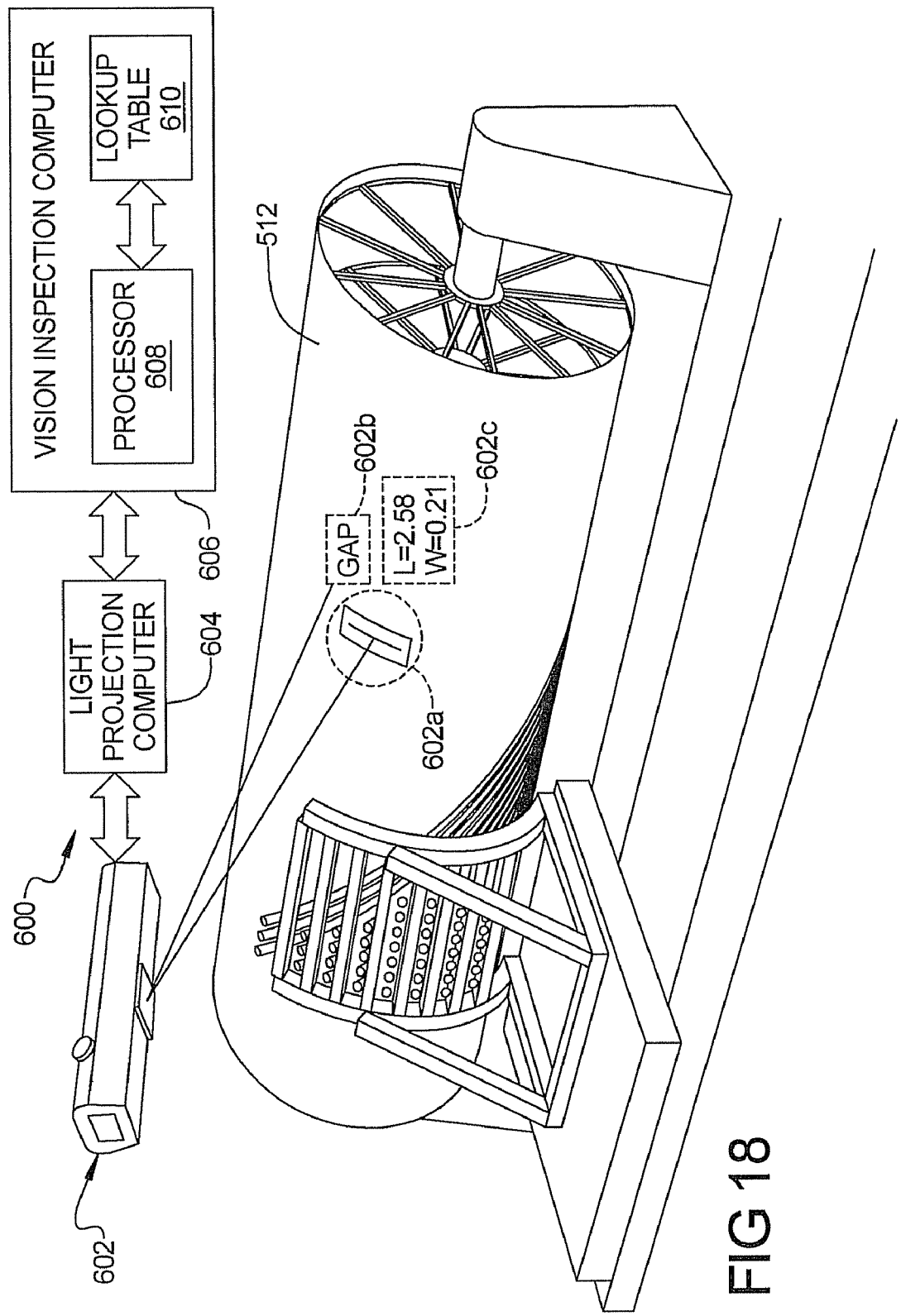
FIG. 18 is another embodiment of the system shown in FIG. 16 that also incorporates the ability to project optical signals onto a composite structure that simultaneously indicate the location of a detected inconsistency, dimensional data regarding the inconsistency taken from the lookup table, and the specific type of inconsistency present.

FIG. 18 illustrates a system 600 in accordance with another embodiment of the present disclosure. The system 600 is similar to the system 500 and common components are represented by reference numerals increased by 100 over those used in connection with the system 500. The system 600 also includes a light source 602 that projects an optical signal illuminating the inconsistency 602a, information concerning the specific type of inconsistency 602b, as well as information 602c from a lookup table 610 representing the dimensions of the detected inconsistency. Preferably, the information 602c is also projected on the composite structure 512 at a location closely adjacent to the information 602b, but this is not absolutely necessary. Thus, the user is apprised of the exact location of the inconsistency by a first optical signal, the specific type of inconsistency that is present via a second optical signal, and the dimensional characteristics of the inconsistency via a third optical signal.

Figure 19:
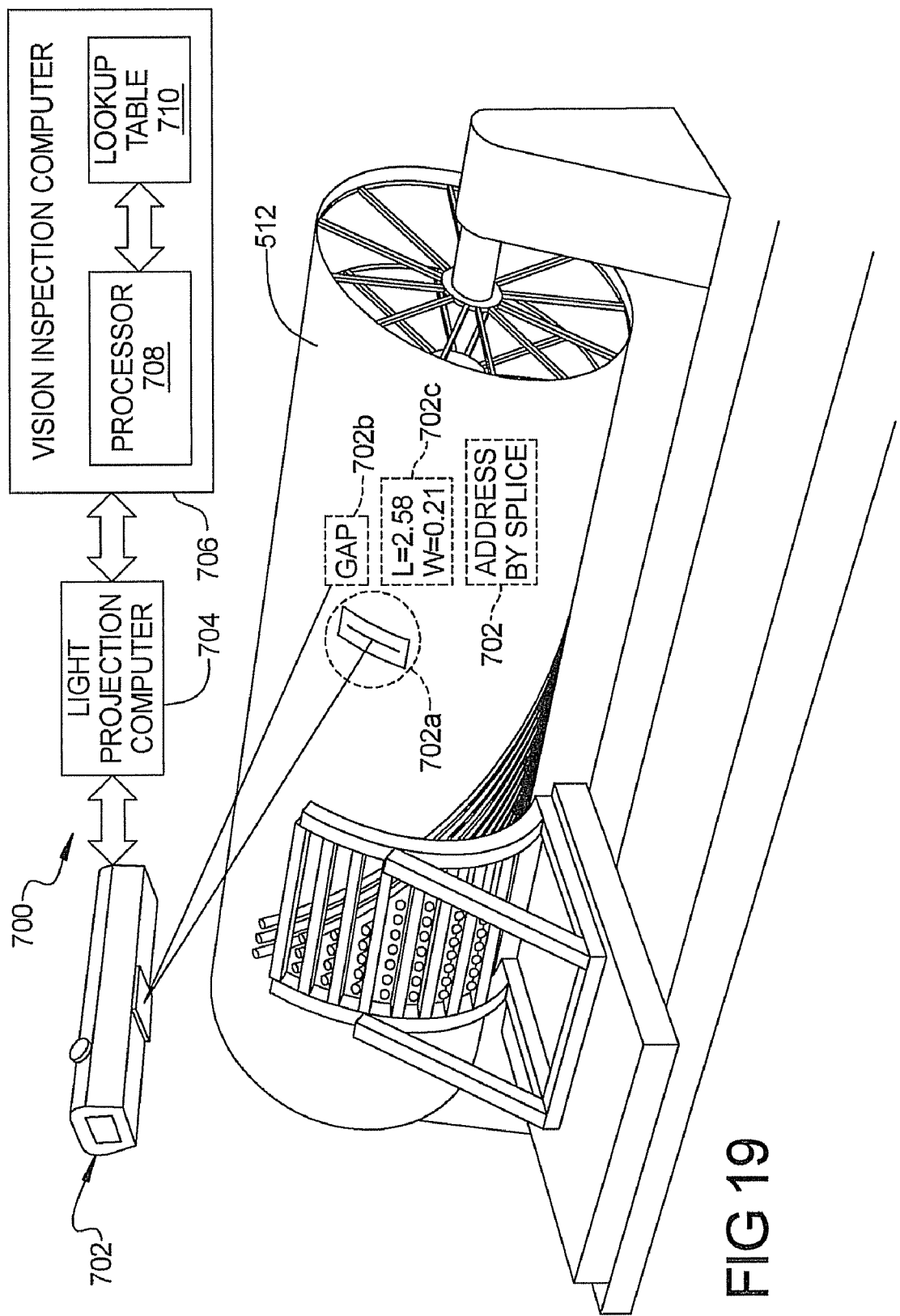
FIG. 19 is another embodiment of the system shown in FIG. 16 that also includes the ability to project an optical signal onto a composite structure that simultaneously indicates the location of the inconsistency, its dimensions, the specific type of inconsistency present, and a suggested method of addressing the inconsistency.
Figure 20:
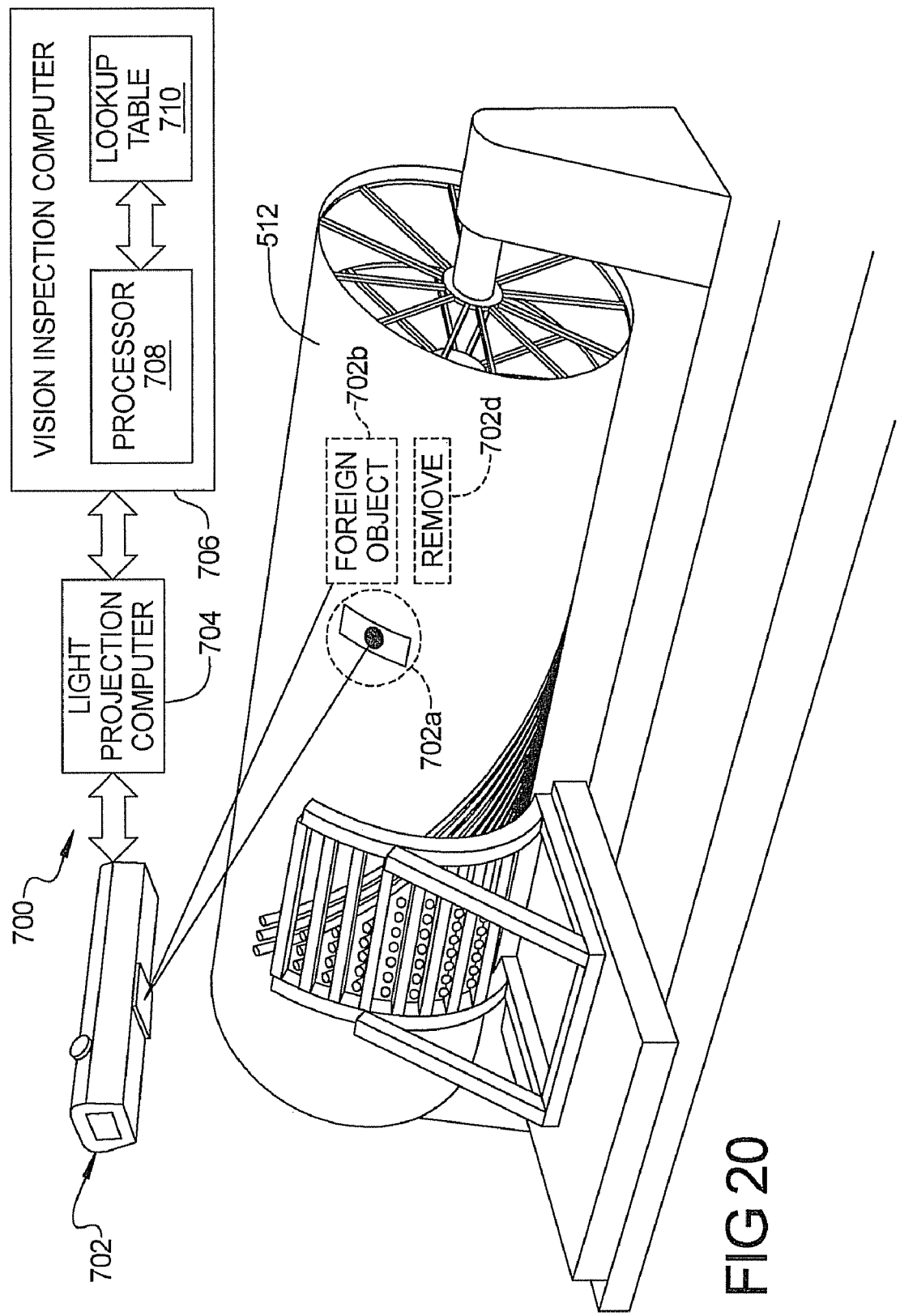
FIG. 20 illustrates the embodiment of FIG. 19 in which information is being projected onto the composite structure indicating the location of the inconsistency, the specific type of inconsistency and the recommended action to address the inconsistency.

FIG. 19 illustrates yet another system 700 in accordance with another embodiment of the present disclosure. The system 700 is similar to the system 500 and common components are denoted by reference numerals increased by 200 over those used in FIG. 16. The system 700 in this embodiment includes an even further sophisticated lookup table 710 that stores information developed from a history of actions addressing various forms of inconsistencies. Such a history may include actions to address a specific consistency in a manner that removes it from the composite structure. The lookup table 710 also includes engineering and/or evaluation results that have been stored pertaining to various types of inconsistencies that have been addressed in the past, from which a probability of successfully addressing the presently detected inconsistency can be determined. The processor 708 of the vision inspection system 706 obtains the information from the lookup table 710 and uses this information to generate signals to the light projection computer 704. These signals are used to generate one or more optical beams that 1) illuminate the inconsistency 702a; 2) indicate the type of inconsistency 702b; 3); illustrate the dimensions of the inconsistency 702c; and 4) provide a suggested action for addressing the inconsistency (e.g., "Splice") as indicated by circled area 710d. The suggested action is based on historical information obtained from the lookup table 710 that indicates what type of action is most appropriate for the specific inconsistency being addressed. FIG. 20 shows the system 700 with the suggested action being indicated in the circled area 702d as "REMOVE".

Figure 21:
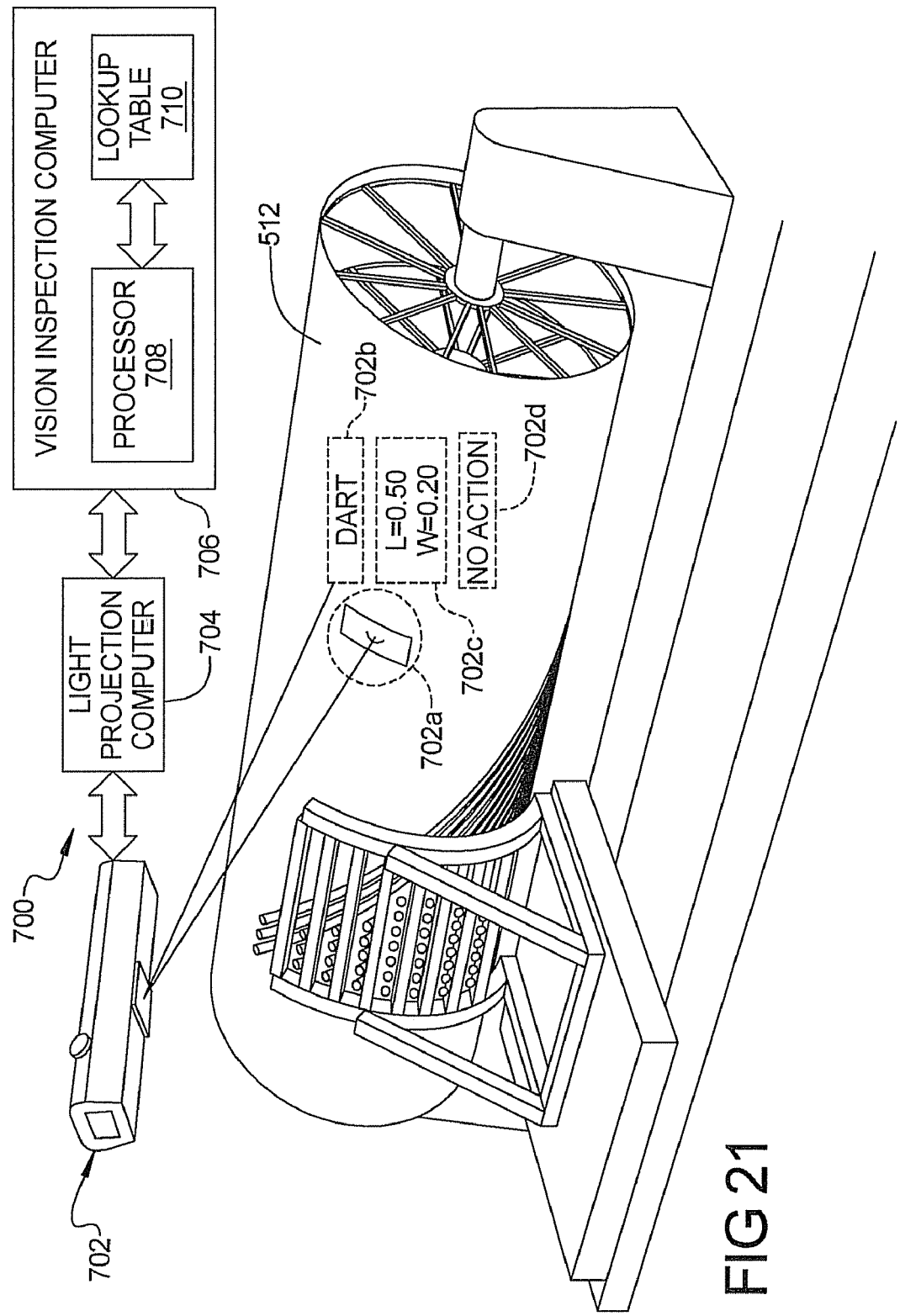
FIG. 21 illustrates the embodiment of FIG. 19 in which information is being projected onto the composite structure indicating the location of the detected inconsistency, the specific type of inconsistency, the dimensions of the inconsistency, and that no action needs to be taken to address the inconsistency.

FIG. 21 shows the system 700 with the suggested action being indicated as "NO ACTION" in the circled area 710d. This may be especially useful because for certain types of inconsistencies, the historical information recorded in the lookup table 710 may indicate that no intervention is actually needed, whereas the user might believe that some intervention is required to address the inconsistency. Thus, this feature may save significant manufacturing time and cost when constructing the composite structure 512.

Various implementations of the disclosure are applicable to a wide range of material placement processes, such as fiber placement, tape placement and fabric placement processes, among others. Accordingly, the specific references to fiber placement herein should not be construed as limiting the scope of the present disclosure to only one specific form/type of material placement process.

While various preferred embodiments have been described, those skilled in the art will recognize modifications or variations which might be made without departing from the inventive concept. The examples illustrate the disclosure and are not intended to limit it. Therefore, the description and claims should be interpreted liberally with only such limitation as is necessary in view of the pertinent prior art.

What is claimed is:

1. A method for indicating inconsistency locations on a composite structure, the method comprising:
   electronically accessing positional data upon receipt of an inconsistency signal from an inconsistency detection system, the positional data defining an inconsistency location of an inconsistency on a composite structure;
   determining whether the inconsistency is unacceptable;
   determining whether the inconsistency can be removed using an automated system;
   determining whether the inconsistency requires manual intervention by an operator; and automatically causing a light source to direct light at the composite structure to indicate:
      the inconsistency location as defined by the positional data;
      whether the inconsistency is unacceptable; and
      if the inconsistency is determined to be unacceptable, at least one of: whether removal of the inconsistency can be automatically affected; and
      whether the inconsistency requires manually effected interaction by a user;
   wherein the electronically accessing includes extracting the positional data from a part fabrication file, the part fabrication file including numerical control (NC) data for a material placement machine to fabricate the composite structure.

2. The method of claim 1, wherein the electronically accessing includes receiving a signal indicating detection of an inconsistency by an inspection system inspecting the composite structure for inconsistencies, and extracting the positional data from the part fabrication file in response to the received signal.

3. The method of claim 2, wherein:
   the electronically accessing includes, upon completion of a ply of the composite structure by the material placement machine, accessing the extracted positional data defining inconsistency locations on the completed ply; and
   the automatically causing including automatically causing the light source to direct light at the completed ply to indicate the inconsistency locations on the completed ply.

4. The method of claim 1, wherein the automatically causing includes creating a program to automatically generate instructions, in connection with the positional data, for automatically causing the light source to direct light at the composite structure to indicate the inconsistency location.

5. The method of claim 1, wherein the automatically causing includes, upon completion of a ply of the composite structure by a material placement machine, automatically causing the light source to direct light at the completed ply of the composite structure to indicate the inconsistency locations on the completed ply.

6. The method of claim 1, wherein the automatically causing includes automatically causing the light source to direct light at the location to illuminate the inconsistency location.

7. The method of claim 1, wherein the light source comprises a laser.

8. The method of claim 7, wherein the automatically causing includes automatically splitting the light emitted by the laser to indicate a plurality of inconsistency locations on the composite structure.

9. The method of claim 1, wherein the automatically causing includes using light to indicate and distinguish among one or more different types of inconsistencies.

10. The method of claim 1, wherein the automatically causing includes using light to indicate and distinguish among one or more different categories of acceptance criteria for inconsistencies.

11. The method of claim 1, wherein the automatically causing includes having the light source direct light at the composite structure to indicate the inconsistency location at least until the inconsistency at the inconsistency location is addressed.

12. The method of claim 1, wherein the automatically causing includes indicating one or more inconsistency locations within a region on the composite structure by having the light source direct light to indicate the region.

13. The method of claim 1, wherein the automatically causing includes accessing a lookup table to obtain stored information concerning and projecting light onto said composite structure that indicates to a user at least one of:
   a specific type of inconsistency that has been encountered;
   dimensional information for a detected inconsistency; and
   a specific recommended action for addressing the inconsistency.

14. The method of claim 1, wherein the automatically causing the light source includes automatically causing the light source to project at least one optical signal onto the composite structure that visually indicates to the user at least two information components, projected to be closely adjacent one another on the composite structure, of the following information components:
   a specific type of inconsistency;
   dimensional information for a detected inconsistency; and
   a recommended action for addressing the detected inconsistency.

15. A system for indicating inconsistency locations on a composite structure, the system comprising:
   at least one light source;
   a controller associated with the light source to control operation of the light source;
   a computer-readable media including instructions executable by the controller for:
   electronically accessing positional data upon receipt of an inconsistency signal from a composite structure inspection system, the positional data defining an inconsistency location of an inconsistency on a composite structure;
   determining whether the inconsistency is unacceptable;
   determining whether removal of the inconsistency can be effected using an automated system;
   determining whether the inconsistency requires manually intervention to address; and
   automatically generating instructions for automatically causing the controller to operate the light source such that the light source directs light at the composite structure to indicate:
      the inconsistency location as defined by the positional data; whether the inconsistency is unacceptable; and
      if the inconsistency is determined to be unacceptable, at least one of:
      whether reworking of the inconsistency can be automatically affected; and whether the inconsistency requires manual interaction by a user to remove;

wherein the computer-readable media further includes instructions executable by the controller for extracting the positional data from a part fabrication file including numerical control (NC) data for a material placement machine to fabricate the composite structure.

16. The system of claim 15, wherein the computer-readable media further includes instructions executable by the controller for receiving a signal indicating detection of an inconsistency by an inspection system inspecting the composite structure for inconsistencies, and wherein the positional data is extracted from the part fabrication file in response to the received signal.

17. The system of claim 15, wherein the computer-readable media further includes instructions executable by the controller for:

accessing upon completion of a ply of the composite structure by the material placement machine, the extracted positional data defining inconsistency locations on the completed ply; and wherein the controller operates the light source such that the light source directs light at the completed ply to indicate the inconsistency locations on the completed ply.

18. The system of claim 16, wherein the controller operates the light source, upon completion of a ply of the composite structure by a material placement machine, such that the light source directs light at the completed ply to indicate the inconsistency locations on the completed ply.

19. The system of claim 15, wherein the light source comprises a laser.

20. The system of claim 19, further comprising a light-splitting device to split the light emitted by the laser to indicate a plurality of inconsistency locations on the composite structure.

21. The system of claim 15, wherein the computer-readable media further includes instructions executable by the controller for communicating with a material placement machine fabricating the composite structure.

22. A program comprising computer-readable media having stored thereon instructions executable by a processor for:

electronically accessing positional data upon receipt of an inconsistency signal from a composite structure inspection system, the positional data defining an inconsistency location of an inconsistency on a composite structure;

determining whether the inconsistency is unacceptable;

determining whether removal of the inconsistency can be effected using an automated system;

determining whether the inconsistency requires manual intervention by a user to remove the inconsistency; and automatically generating instructions for automatically causing a light source to direct light at the composite structure to indicate:

the inconsistency location as defined by the positional data;

whether the inconsistency is unacceptable; and if the inconsistency is determined to be unacceptable, at least one of:

whether removal of the inconsistency can be automatically effected; and whether the inconsistency requires manually interaction by a user to effect removal of the inconsistency;

wherein the computer-readable media further has stored thereon instructions executable by the controller further comprising for extracting the positional data from a part fabrication file, the part fabrication file including numerical control (NC) data for a material placement machine to fabricate the composite structure.

23. The program of claim 22, wherein the computer-readable media further has stored thereon instructions executable by the controller for receiving a signal indicating detection of an inconsistency by an inspection system inspecting the composite structure for inconsistencies, and wherein the positional data is extracted from the part fabrication file in response to the received signal.

24. The program of claim 23, wherein the computer-readable media further has stored thereon instructions executable by the controller for accessing, upon completion of a ply of the composite structure by the material placement machine, the extracted positional data defining inconsistency locations on the completed ply, and wherein the instructions automatically cause the light source to direct light at the completed ply to indicate the inconsistency locations on the completed ply.

25. The program of claim 24, wherein the computer-readable media further has stored thereon instructions executable by the controller for communicating with a material placement machine fabricating the composite structure.

26. A method for indicating inconsistency locations on a composite structure, the method comprising:

electronically accessing positional data upon receipt of an inconsistency signal from an inconsistency detection system, the positional data defining an inconsistency location of an inconsistency on a composite structure;

determining whether the inconsistency is unacceptable;

determining whether the inconsistency can be removed using an automated system;

determining whether the inconsistency requires manual intervention by an operator; and automatically obtaining information from a lookup table and using the information to cause a light source to direct light at the composite structure to provide optical signals that simultaneously indicate:

the inconsistency location as defined by the positional data; and a specific type of inconsistency that is present on the composite structure;

wherein the electronically accessing includes extracting the positional data from a part fabrication file, the part fabrication file including numerical control (NC) data for a material placement machine to fabricate the composite structure.

27. The method of claim 26, wherein the optical signals further comprise information that indicates at least one of;

dimensions of each inconsistency detected; and a recommended course of action for each inconsistency detected.

* * * * *